(12) United States Patent
Kitagawa et al.

(10) Patent No.: US 7,009,066 B2
(45) Date of Patent: Mar. 7, 2006

(54) POROUS COORDINATIVELY UNSATURATED METAL COMPLEX

(75) Inventors: Susumu Kitagawa, Neyagawa (JP); Hiroshi Yamamoto, Kobe (JP); Jun Tatsumi, Ikoma (JP)

(73) Assignee: Nippon Shokubai Co., Ltd., Osaka (JP)

( * ) Notice: Subject to any disclaimer, the term of this patent is extended or adjusted under 35 U.S.C. 154(b) by 24 days.

(21) Appl. No.: 10/437,294

(22) Filed: May 14, 2003

(65) Prior Publication Data

US 2004/0014598 A1    Jan. 22, 2004

(30) Foreign Application Priority Data

May 15, 2002 (JP) ............................. 2002-140495
Jan. 31, 2003 (JP) ............................. 2003-025182

(51) Int. Cl.
C07F 1/08 (2006.01)
C07F 9/00 (2006.01)
C07F 15/00 (2006.01)
B01J 31/00 (2006.01)

(52) U.S. Cl. .................... 556/32; 502/150; 502/162
(58) Field of Classification Search .................. 556/32; 502/150, 162
See application file for complete search history.

(56) References Cited

U.S. PATENT DOCUMENTS 4,113,759 A * 9/1978 Papenfuhs et al. ............ 556/34
5,648,508 A 7/1997 Yaghi ............................. 556/9

FOREIGN PATENT DOCUMENTS

| EP | 0 583 748 | 2/1994 |
| JP | 9-227572 | 9/1997 |
| JP | 2000-178279 | 6/2000 |
| JP | 2000-309592 | 11/2000 |

OTHER PUBLICATIONS

H.B. Song et al., "2,6-Bis(diphenylphosphino)pyridine-bridged hetero-polynuclear complexes consolidated by Fe→M (M=Ag, Hg) dative bonding", Inorganic Chemistry, vol. 40, No. 23, Nov. 9, 2001, pp. 5928-5933, XP002246396.

N. Bricklebank et al., "Structure of diiodine adducts of some di- and tri-tertiary phosphines in the solid state and in solution", Journal of the Chemical Society, Dalton Transactions, No. 14, 1998, pp. 2379-2382, XP002246397.

M.A. Whitener et al., "3-[(2-Aminoethyl)iminomethyl]-4-hydroxy-benzoic Acid 0.28-Hydrate", Acta Crystallographica, vol. c54, 1998, pp. 1119-1121, XP009013278.

B. Dash et al., "Thiazolidone Derivatives", Journal of the Indian Chemical Society, vol. 58, Dec. 1981, pp. 1184-1186, XP009013229.

R.S. Downing et al., "Circular Dichroism of Square-Planar, Tetradentate Schiff-Base Chelates of Nickel(II)", Journal of the American Chemical Society, vol. 92, No. 20, Oct. 7, 1970, pp. 5861-5865, XP002246398.

(Continued)

Primary Examiner—Porfirio Nazario-Gonzalez
(74) Attorney, Agent, or Firm—Wenderoth, Lind & Ponack, L.L.P.

(57) ABSTRACT

A porous coordinatively unsaturated metal complex comprises metal complex units. Each metal complex unit includes a first metal and an organic ligand. The metal complex units are connected one another through a second metal (a connecting metal). The porous coordinatively unsaturated metal complex has voids formed by the connection. Voids have a size of 10 Å or more. The first metal is rendered to a coordinatively unsaturated state in the metal complex unit. With this arrangement, not only low-molecular weight compounds but also general compounds can be introduced as substrates. Further, the porous coordinatively unsaturated metal complex has high catalytic activity or high molecule retainability.

5 Claims, 10 Drawing Sheets

→ COORDINATION ACCEPTOR SITE

⇨ COORDINATION DONOR SITE

OTHER PUBLICATIONS

L.N. Ferguson et al., "Chelation and Association of Some Ethylenediamine Schiff Bases[1]", Journal of the American Chemical Society, vol. 73, No. 8, Aug. 1951, pp. 3707-3709, XP002246399.

M. Calvin et al., "Stability of Chelate Compounds. V. The o-Formylnaphthoxide Chelates[1]", Journal of the American Chemical Society, vol. 70, No. 10, Oct. 1948, pp. 3273-3275, XP002246400.

M. Fujita et al., "Preparation, Clathration Ability, and Catalysis of a Two-Dimensional Square Network Material Composed of Cadmium(II) and 4,4'-Bipyridine", Journal of the American Chemical Society, vol. 116, No. 3, Feb. 9, 1994, pp. 1151-1152, XP002246403.

R.H. Bailes et al., "The Oxygen-Carrying Synthetic Chelate Compounds. VII. Preparation", Journal of the American Chemical Society, American Chemical Society, vol. 69, Aug. 1, 1947, pp. 1886-1893, XP000611957.

C.C. Cheng et al., "Novel Water-Soluble 4,4-Disubstituted Ruthenium(III)-Salen Complexes in DNA Stranded Scission", Journal of the Chinese Chemical Society, vol. 45, 1998, pp. 611-617, XP009013097.

* cited by examiner

CONCEPTUAL DIAGRAM OF METAL COMPLEX UNIT

➡ COORDINATION ACCEPTOR SITE
⇨ COORDINATION DONOR SITE

FIG.3
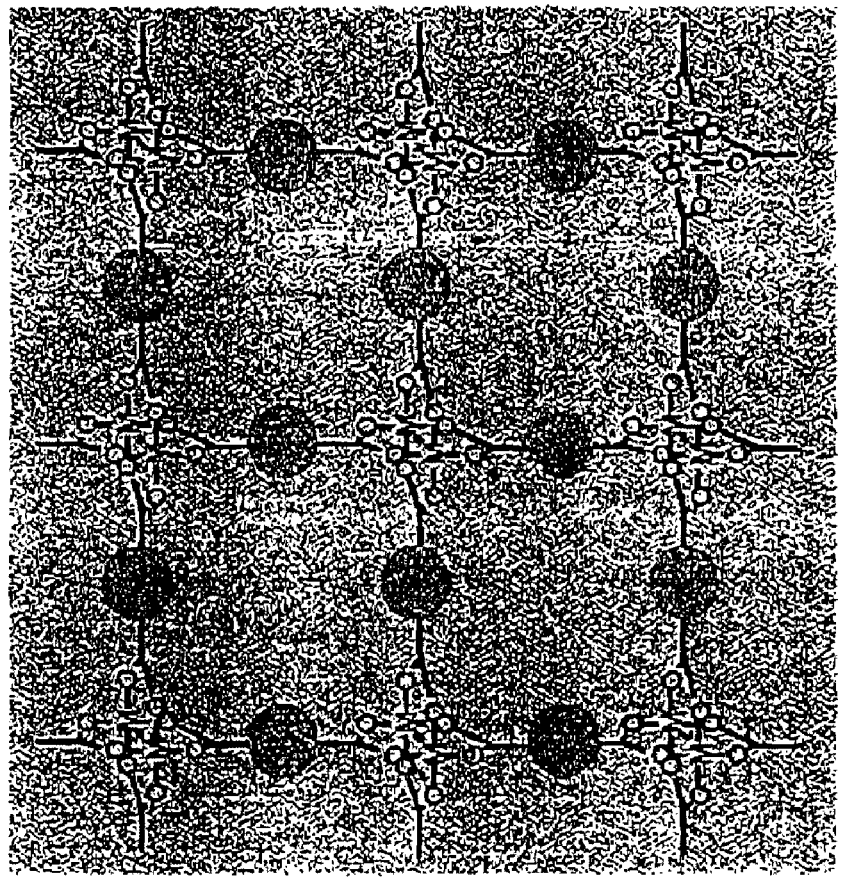
SCHEMATIC DIAGRAM OF POROUS COORDINATIVELY UNSATURATED METAL
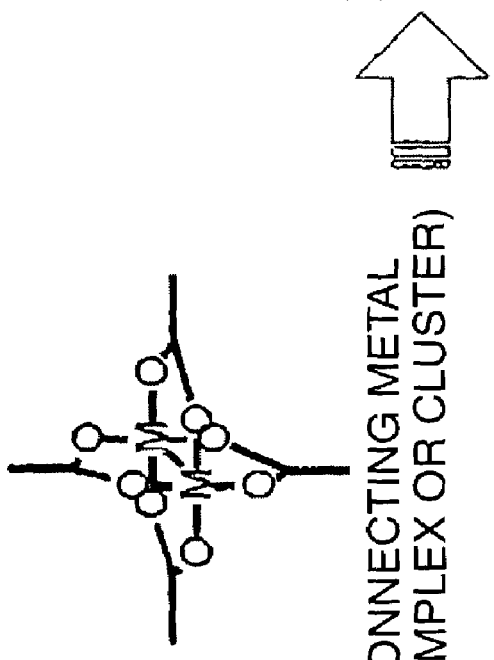
CONNECTING METAL (COMPLEX OR CLUSTER)
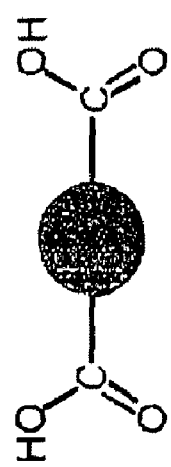
METAL COMPLEX UNIT

RESULT OF THERMOGRAVIMETRY

POROUS COORDINATIVELY UNSATURATED METAL COMPLEX

BACKGROUND OF THE INVENTION

1. Field of the Invention

This invention relates to a porous coordinatively unsaturated metal complex in which a number of metal complex units are connected one another by connecting metals, and a process for producing such a metal complex. Further, this invention pertains to a compound usable as a metal complex unit and an organic ligand as component substances constituting the porous coordinatively unsaturated metal complex.

2. Description of the Related Art

Metal complex is a composite of a ligand and a metal. Metal complex exhibits high catalytic activity, and provides an optimal field for reaction. Metal complex exhibits such properties based on the premise that a metal having high reactivity and accordingly being labile stays stably in a metal complex and that a ligand has a specific conformation. Since metal complex has high usability, study concerning metal complex has been conducted in many fields.

For instance, there is known an approach regarding a "coordinatively unsaturated metal complex" in which a metal capable of making coordination bonding at plural positions or sites is supported in a complex in a so-called "coordinatively unsaturated state", namely, in a state that a ligand is not coordinatively bound to the positions or sites where it is supposed to be coordinatively bound. Such a coordinatively unsaturated metal complex exhibits high chemical reactivity because the metal in the complex is coordinatively unsaturated. That is, it is inherently difficult for the metal to stay stably due to its high reactivity. However, the metal can be rendered stable in the complex in a coordinatively unsaturated state by devising a ligand, thereby making it possible to provide the metal complex with high catalytic activity.

Coordinatively unsaturated metal complexes having voids are described in (1) B. Chen, et al., "$Cu_2(ATC) \cdot 6H_2O$: Design of Open Metal Sites in Porous Metal—Organic Crystals (ATC:1,3,5,7-Adamantane Tetracarboxylate)", J. Am. Chem. Soc., 122, pp. 11559–11560 (2000) and (2) M. Eddaoudi, et al., "Modular Chemistry: Secondary Building Units as a Basis for the Design of Highly Porous and Robust Metal—Organic Carboxylate Frameworks", Acc. Chem. Res., 34, pp. 319–330 (2001). These references suggest that the coordinatively unsaturated metal complexes are usable in storage of specific compounds or the like.

However, according to the above paper (1), whereas the metal complex is capable of readily incorporating $CH_2Cl_2$, it is incapable of readily incorporating $C_6H_6$, $CCl_4$, $C_6H_{12}$. This shows that the substrate intended to be incorporated in the metal complex recited in these papers (1) and (2) is limited to low-molecular weight compounds.

And in the reference (3) S. Noro, et al., "New microvoid coordination polymer affording guest-coordination sites at channel walls, Chem. Comm., pp. 222–223 (2002), a porous metal complex in which a coordinatively unsaturated metal is coordinatively bound to a wall of a polyhedron defining a cavity of the metal complex instead of a vertex of a polyhedron.

But reference (3) recites that the size of the cavity in the metal complex is 15×5 Å, and accordingly, it can be concluded that the cavity has a slit-like shape rather than a void. Therefore, the metal complex having such slit-like cavities fails to incorporate a general compound as a substrate, although it can incorporate a low-molecular weight compound. Actually, what is recited in reference (3) as substrate molecules (compounds to be incorporated) is nothing more than dimethylformamide (DMF) and water molecules.

As mentioned above, academic approaches have been conducted primarily in the field of porous metal complexes because the configuration of porous metal complexes has provided intriguing topic for the researchers. There has also been proposed a technology of actually applying such a metal complex. For example, (4) Japanese Unexamined Patent Publication No.9-227571 discloses a metal complex having cavities of a predetermined size and capable of incorporating and holding specific molecules. The metal complex disclosed in reference (4) has cavities of a predetermined size resulting from its multi-layered structure constructed such that layers having a specific structure are linked one over another by way of component substances, and thus exhibits properties capable of incorporating specific molecules into the cavities. However, since the cavities of the complex are extremely narrow, the metal complex can incorporate merely small molecules such as oxygen and methane gas. Furthermore, since a metal ion as a component substance is in a so-called "coordinatively saturated state", the metal complex incorporated with such a metal ion fails to exhibit high catalytic activity.

In addition to the aforementioned drawbacks, some of the conventional porous metal complexes are constructed by hydrogen bonding. Accordingly, they fail to provide rigidity such as stability.

There have been known organic ligands of salen type, as component substances of a metal complex. For instance, a ruthenium-based coordinatively unsaturated complex of salen type is disclosed in (5) C—C. Cheng, et al., "Novel Water-Soluble 4-4-Disubstituted Ruthenium (III)-Salen Complexes in DNA Stranded Scission, J. Chin. Chem. Soc., 45, pp. 611–617 (1998). This reference (5) discloses that the metal complex breaks DNA chain along with hydrogen peroxide. However, reference (5) neither discloses nor remotely suggests forming a porous metal complex with use of an organic ligand of salen type.

Despite the aforementioned knowledge, the prior art fails to find out a porous coordinatively unsaturated metal complex that enables to incorporate not only low-molecular weight compounds but also general compounds as substrates and enables to exhibit high catalytic activity.

SUMMARY OF THE INVENTION

In view of the above problems residing in the prior art, it is an object of this invention to provide a porous coordinatively unsaturated metal complex having voids of a certain size that enables to incorporate not only low-molecular weight compounds but also general compounds as substrates, and enables to exhibit high chemical activity because a coordinatively unsaturated metal as a component is capable of sufficiently exhibiting its function, and a process for producing such a metal complex.

It is another object of this invention to provide use of such a metal complex as a catalyst, and a metal complex unit and an organic ligand adapted for forming such a metal complex.

According to an aspect of this invention, provided is a porous coordinatively unsaturated metal complex comprising: a number of metal complex units and second metals, the each metal complex unit including a first metal and an organic ligand, the first metal being rendered to a coordinatively unsaturated state in the metal complex unit, the porous coordinatively unsaturated metal complex being structured by connecting the metal complex units one another through the second metals; the porous coordinatively unsaturated metal complex having voids; the voids having a size of 10 Å or more.

The above porous coordinatively unsaturated metal complex has a feature that the coordinatively unsaturated metals are arrayed regularly. With this arrangement, a substrate having a certain reactivity (or reactive substrate) can be selected optimally and used for a desired reaction. In addition, since the voids formed in the metal complex are relatively large, large molecules as well as small molecules such as oxygen and methane gas can be selectively incorporated in the metal complex. Further, the coordinatively unsaturated metal has such an action that enables to allow the incorporated molecule to exhibit catalytic activity or enables to securely hold the incorporated molecule at the incorporated position or site.

Thus, the porous coordinatively unsaturated metal complex of this invention is usable as a catalyst having high substrate specificity or a compound having high ability of retaining molecules.

These and other objects, features and advantages of the present invention will become more apparent upon a reading of the following detailed description and accompanying drawing.

BRIEF DESCRIPTION OF THE DRAWINGS

FIG. 3 is an illustration showing how a porous coordinatively unsaturated metal complex in accordance with this invention is formed;

DESCRIPTION OF THE PREFERRED EMBODIMENTS

Figure 1:
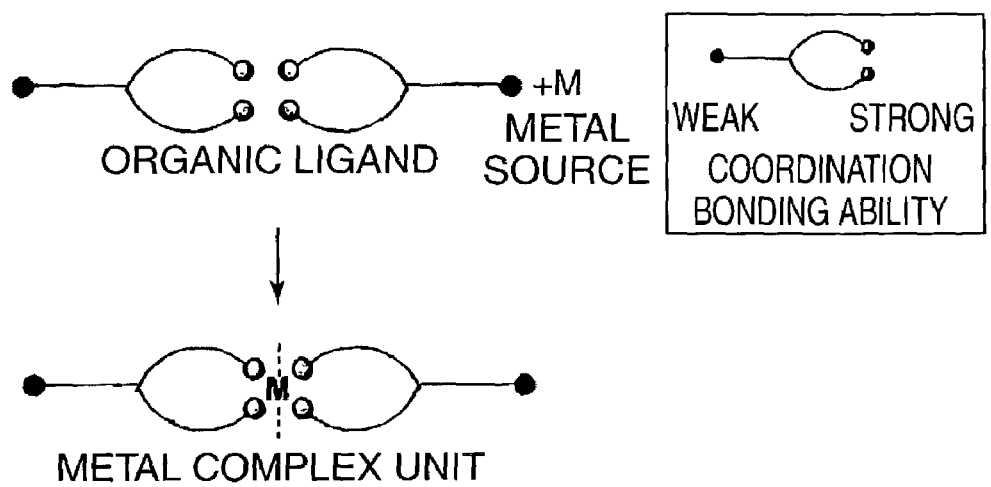
FIG. 1 is a conceptual diagram of a metal complex unit in this invention.

In view of the above problems residing in the prior art, the inventors of the present application have conducted extensive study and research to clarify the conditions that can stably retain a coordinatively unsaturated state of a metal in a porous metal complex, sufficiently exhibit catalytic activity of the complex, and form voids of a sufficient size.

As a result of the extensive study and research, the inventors elucidated that the defects of the prior art that merely layered- or slit-like clearances are formed and that merely compounds of small molecules are usable as substrates or that coordinatively unsaturated metals fail to sufficiently exhibit their catalytic activities result from the fact that both of a metal that is to exhibit catalytic activity and a metal adapted to connect adjacent organic ligands are bound to respective sites of the organic ligand structurally identical to each other. In other words, they have found a technique that supporting a metal (first metal) that is rendered to a coordinatively unsaturated state and exhibits catalytic activity to a certain site of the organic ligand and then connecting the organic ligands at the site (coordination donor site) which is structurally different from the former site coordinatively bound to the first metal by a connecting metal (second metal) facilitates formation of a porous coordinatively unsaturated metal complex constructed such that the coordinatively unsaturated metal is supported on a wall of a void and that the size of the void is sufficiently large in conformance with the size of the organic ligand. Thus, the inventors of this application accomplished this invention.

According to an aspect of this invention, a porous coordinatively unsaturated metal complex of the present invention has the following features:

in which a number of metal complex units each comprised of a metal (first metal) and an organic ligand are connected one another by way of connecting metals (second metal), voids are formed in the coordinatively unsaturated metal complex by the connection, the void has a size of 10 Å or more, and the metal in the metal complex unit is rendered to a coordinatively unsaturated state.

Preferably, the porous coordinatively unsaturated metal complex may be such that at least one site of the organic ligand which coordinates to the first metal is a 15-group element of the periodic table. This is because 15-group elements in the periodic table such as a nitrogen atom and a phosphorous atom have excellent bonding ability to coordinatively bind the metal, and accordingly can stably retain the first metal in a coordinatively unsaturated state in the organic ligand.

Preferably, the compound represented by the formula (I) is optimal as the organic ligand in view of the fact that the compound has excellent bonding ability to coordinatively bind the first metal and accordingly can support the first metal in a coordinatively unsaturated state. Further, Examples, which will be described later, reveal that use of the compound facilitates formation of a metal complex having voids of 10 Å or more in size.

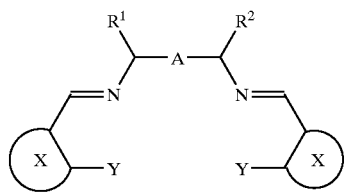

[wherein:

"A" represents a single bond or a double bond, or may be absent;

"X" represents a $C_6$–$C_{10}$ monocyclic or a condensed aromatic hydrocarbon group (which is substituted by 1 to 4 α groups to be described later), or a nitrogen-containing heteroaryl group;

"Y" represents a hydroxyl group, an amino group, a thiol group, a di($C_1$–$C_6$alkyl)amino group, a di($C_1$–$C_6$alkyl)phosphino group, or a diarylphosphino group;

$R^1$ and $R^2$ are identical to or different from each other, represent each a hydrogen atom, a $C_1$–$C_6$alkyl group, a $C_2$–$C_6$alkenyl group, a $C_1$–$C_6$alkoxy group, a halogen atom, a hydroxyl group, an amino group, a nitro group, or a cyano group, or the following partial structure integrally comprised of $R^1$, $R^2$, carbon atoms respectively adjacent thereto, and "A" represents a $C_6$–$C_{22}$ monocyclic or a condensed aromatic hydrocarbon group (which may be substituted by 1 to 4 β groups to be described later) or a $C_3$–$C_6$ cyclic hydrocarbon group (which may be substituted by 1 to 4 β groups to be described later);

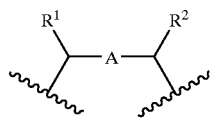

α is a group selected from the group consisting of a carboxyl group, a nitrogen-containing heteroaryl group, a di($C_1$–$C_6$alkyl)phosphino group, a diarylphosphino group, a cyano group, a hydroxyl group, an amino group, and a thiol group; and β is a group selected from the group consisting of a $C_1$–$C_6$alkyl group, a $C_1$–$C_6$alkoxy group, a halogen atom, a hydroxyl group, an amino group, a nitro group, and a cyano group.]

According to another aspect of this invention, a process for producing a porous coordinatively unsaturated metal complex of the present invention, the process comprising steps of reacting the organic ligand with the first metal to prepare the metal complex unit in which the first metal is supported in a coordinatively unsaturated state, the organic ligand having two coordination donors with a distance between the coordination donors of 10 Å or more, and mixing the metal complex units or a solution containing the metal complex units with the second metals or a solution containing the second metals to connect the metal complex units one another through the second metals.

The above process is advantageous in facilitating formation of the porous coordinatively unsaturated metal complex of the present invention in which the coordinatively unsaturated metal is supported on a wall of a void, wherein the void has a predetermined size.

Yet another aspect of this invention is directed to use of the aforementioned porous coordinatively unsaturated metal complex as a catalyst. The use of the porous coordinatively unsaturated metal complex of the present invention is advantageous in the aspect that not only low-molecular weight compounds but also general compounds are usable as reactive substrates and that the resultant metal complex exhibits high catalytic activity.

The metal complex unit in this invention is adapted to form the porous coordinatively unsaturated metal complex of the present invention, and is represented by the following formula (II). As mentioned above, use of the metal complex unit is advantageous in facilitating formation of the coordinatively unsaturated metal complex of this invention.

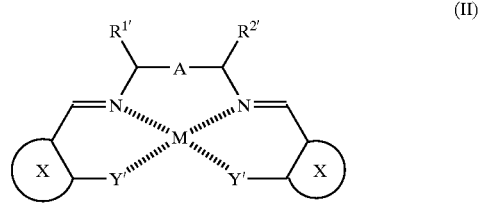

[wherein

A and X are as defined above;

M is a metal element in a coordinatively unsaturated state;

Y' represents an oxygen atom, an NH group, a sulfur atom, a di($C_1$–$C_6$alkyl)amino group, a di($C_1$–$C_6$alkyl)phosphino group, or a diarylphosphino group;

$R^{1'}$ and $R^{2'}$ are identical to or different from each other, are each a hydrogen atom, a $C_1$–$C_6$alkyl group, a $C_2$–$C_6$alkenyl group, a $C_1$–$C_6$alkoxy group, a halogen atom, a hydroxyl group, an amino group, a nitro group, or a cyano group, or the following partial structure integrally comprised of $R^{1'}$, $R^{2'}$, carbon atoms respectively adjacent thereto, and A represents a $C_6$–$C_{22}$ monocyclic or a condensed aromatic hydrocarbon group (which may be substituted by 1 to 4 β groups) or a $C_3$–$C_6$ cyclic hydrocarbon group (which may be substituted by 1 to 4 β groups);

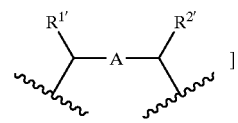

When Y in the organic ligand is a hydroxyl group, an amino group or a thiol group, it is conceived that a hydrogen atom of the hydroxyl group and the like is dissociated and a first metal is bound to the organic ligand in formation of a metal complex unit by coordination bonding. It should be noted that the first metal can be coordinatively bound to a di($C_1$–$C_6$alkyl)amino group, di($C_1$–$C_6$alkyl)phosphino group and diarylphosphino group.

In the definition of $R^{1'}$ and $R^{2'}$, when either one of $R^{1'}$ and $R^{2'}$ is a hydrogen atom, preferably, the other one thereof may not be a hydrogen atom.

The organic ligand in this invention is adapted for constituting the porous coordinatively unsaturated metal complex of the present invention, and is represented by the following formula (III). As mentioned above, the organic ligand is very useful as a component substance constituting the porous coordinatively unsaturated metal complex of the present invention.

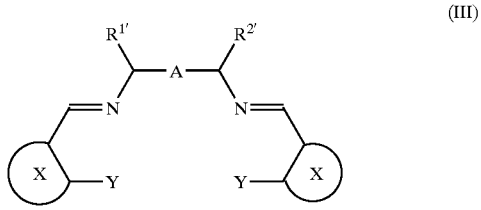

[wherein, A, X, Y, $R^{1'}$ and $R^{2'}$ are as defined above.]

Hereinafter, definitions of the terms used throughout the present specification will be described.

"A metal in a coordinatively unsaturated state" in this invention means that a metal that is unstable, because a ligand is not bound to the metal at a site where it is supposed to be bound and accordingly is liable to be readily bound to a reactive substrate or its equivalent, is retained in a metal complex with a coordination bondable site being left by being coordinatively bound to an organic ligand. "A metal complex unit" in this invention is a unit of a metal complex in which a metal is supported in a coordinatively unsaturated state among a variety of metal complexes in which a specific organic ligand is coordinatively bound to a metal.

The first metal as a component substance constituting the "metal complex unit" in this invention is not specifically limited as far as the metal has a property capable of being rendered to a "coordinatively unsaturated state". Some of the examples of the first metal are V, Cr, Mn, Fe, Co, Ni, Cu, Zn, Nb, Mo, Ru, Rh, Pd, Cd, Ir, Pt, Ti, Zr, Al, and Tl.

Some of the metals such as V, although depending on the kind of transition metal, are stably supported to an organic ligand in a coordinatively saturated state because an oxygen atom or its equivalent are additively and coordinatively bound. In such a case, since π electron between metal-oxygen or its equivalent is attracted to the oxygen atom or its equivalent, the metal is retained in a state analogous to a coordinatively unsaturated state, and has its active state retained. The "metal in a coordinatively unsaturated state" used in this invention includes such a metal that can exhibit properties analogous to a coordinatively unsaturated state.

Also, there is a case that a metal complex is brought to an apparently coordinatively saturated state because a low-molecular weight compound such as water and solvents other than water is coordinatively bound to a coordinatively unsaturated metal. Even in such a case, the metal complex of the present invention exhibits the aforementioned properties by substituting a reactive substrate for water or a low-molecular weight solvent. Such a state analogous to a coordinatively unsaturated state is embraced in the scope of this invention.

Further, it is conceived that the active state of a metal complex is improved by temporarily coordinatively binding a compound enriched with electrons such as a nitrogen-containing heteroaryl solvent to at least one of the plurality of positions (site) available for coordination bond (coordination-bondable site) of the coordinatively unsaturated metal.

The first metal in the "metal complex unit" may be such that at least a moiety of the metal is in a coordinatively unsaturated state (including the aforementioned analogously coordinatively unsaturated state). Preferably, 20% or more, further preferably 50% or more, furthermore preferably 80% or more, and optimally 90% or more of the metal may be in a coordinatively unsaturated state. This is because a coordinatively unsaturated metal has high activity as compared with a case of a coordinatively saturated metal.

It is conceived that the metal in the "metal complex unit" is in an ionized state or in a state of an atom. Both of the states are embraced in this invention.

Generally, a "ligand" is a molecule or a molecule group capable of being coordinatively bound to a central atom (metal or metal ion) in a metal complex. An "organic ligand" of this invention is at least one or more organic compounds to which a first metal (including a metal ion) can be coordinatively bound and can stably retain the first metal in a coordinatively unsaturated state.

In this invention, a compound comprised of a coordinatively unsaturated metal and an organic ligand is referred to as a "metal complex unit". The "metal complex unit" has a position (site) capable of rendering a first metal to a substantially coordinatively unsaturated state, and thereby making it possible for the metal complex unit to exhibit catalytic activity. Furthermore, according to this invention, since the metal complex unit has an atom or an atom group (coordination donor) capable of performing at least two or more of chemical bonds, the porous coordinatively unsaturated metal complex of this invention is producible by connecting a number of the metal complex units by way of "connecting metals", which will be described later. The "chemical bonds" in this context are coordination bond, covalent bond, and ion bond. It should be appreciated, however, that labile bonds such as hydrogen bond, which may be additionally formed, may be embraced in this invention.

An "organic ligand" in this invention has a feature that the chemical structures of a site for supporting a coordinatively unsaturated metal and a site for binding a connecting metal (coordination donor site) are different from each other. This arrangement makes it possible to allow the moiety of the organic ligand used for supporting the coordinatively unsaturated metal and the moiety thereof used for binding the connecting metal to function differently and to secure a sufficiently large distance between the coordination donors in the organic ligand in conformance with the size of a void of the porous coordinatively unsaturated metal complex. This arrangement obviates a likelihood that a metal which is supposed to exhibit catalytic activity may be used for connecting organic ligands, which enables to improve chemical activity of the metal.

Figure 2:
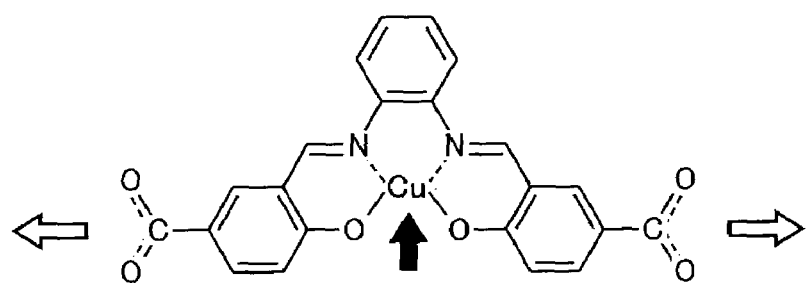
FIG. 2 is an illustration explaining a coordination acceptor site and a coordination donor site in the metal complex unit in this invention.

FIG. 1 is a conceptual diagram of the "metal complex unit" in this invention. The "metal complex unit" in this invention is not limited to what is disclosed in the above or in the drawings attached to this specification. FIG. 2 is an illustration showing a "coordination acceptor site" of a metal which is a site adapted to coordinatively bind a reactive substrate, and a "coordination donor site" of the unit which is a site adapted to connect adjacent metal complex units via a "connecting metal" to be described later.

The "connecting metal" (the second metal in the porous coordinatively unsaturated metal complex) in this invention is a metal capable of connecting two or more of the "metal complex units" of this invention adjacent to each other or one another by coordination bond or ion bond. The "connecting metal" may be such that it forms a complex in combination with other compound, as well as a metal or a metal ion, as far as the connecting metal can exhibit the aforementioned actions and effects. The connecting metal may form a cluster.

FIG. 3 is an illustration showing a porous coordinatively unsaturated metal complex in which a number of metal complex units are connected one another by way of the connecting metals. The porous coordinatively unsaturated metal complex of this invention is not limited to what is disclosed in the above or in the drawings attached to this specification.

Some of the examples of the metal which directly exhibit a connecting function as the "connecting metal" are Zn and Cu. Alternatively, a general metal may be used without constraint. Use of the same kind of metal element as the coordinatively unsaturated metal (first metal) as the connecting metal may be convenient in the aspect of preparing a complex. However, using the different kind of metal element from the coordinatively unsaturated metal as the connecting metal enables to provide a variety in structure, reaction, and the like. In preparing the porous coordinatively unsaturated metal complex of this invention, a metal constituting the "connecting metal" is added in an ionized state, and it is conceived that the connecting metal may be bound to an organic ligand in an ionized state or in a state of an atom (metal) in formation of the porous coordinatively unsaturated metal complex. Both of the states are embraced in this invention. In this way, selecting a suitable metal among a variety of "connecting metals" as component substances makes it possible to provide the porous coordinatively unsaturated metal complex of this invention with various actions and effects. It should be appreciated that the case that the "connecting metal" is in a coordinatively unsaturated state may be embraced in this invention.

The "porous coordinatively unsaturated metal" of this invention is a porous material obtained by connecting the aforementioned "metal complex units" one another by the "connecting metals", in which a multitude of voids are formed.

The size of the void is determined depending on the kind and dimensions of the "metal complex unit" and the "connecting metal ". Setting the size or dimensions of the voids provides the resultant porous coordinatively unsaturated metal with selectivity in incorporating substrate molecules.

Preferably, the "porous coordinatively unsaturated metal complex" of this invention may be such that the "coordinatively unsaturated metals" in the "metal complex units" are arrayed regularly or with a certain regularity. The alignment of the metals at a certain interval allows a substrate molecule to be bound to a corresponding coordinatively unsaturated metal along a predetermined orientation. Thereby, stereoselective control can be implemented in various chemical reactions such as oxidation, reduction, and polymerization reaction of olefins. Further, aligning the coordinatively unsaturated metals regularly at a predetermined interval or more enables to prevent chemical activity of the metal complex from lowering due to metal-metal bond owing to existence of oxygen and the like. This technique is applicable to a reaction such as tandem reaction or cascade reaction which requires setting a certain distance between substrate-substrate. Conversely, aligning the coordinatively unsaturated metals regularly at a predetermined interval or less enables to coordinatively bind one substrate to two coordinatively unsaturated metals. This arrangement makes it possible to catalyze a specific chemical reaction such as C-alkylation of an amino acid.

"Crystal" is known as an example of structural systems. Crystal is a solid substance in which atoms are arrayed cyclically in a space lattice. Such a space lattice" seen in the structural system in crystal is not the void defined in this invention.

Figure 4:
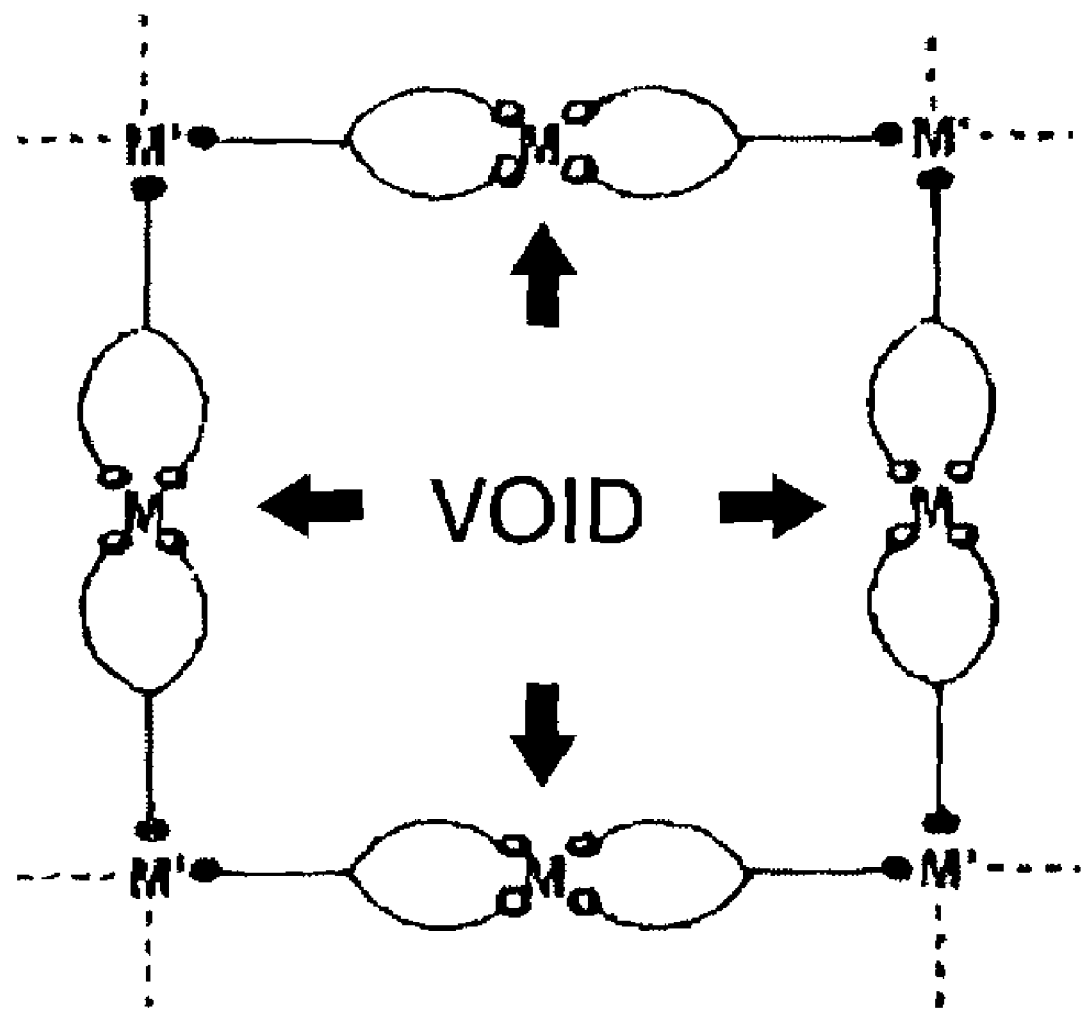
FIG. 4 is an illustration showing a void formed in the porous coordinatively unsaturated metal complex of this invention.

FIG. 4 is an illustration of the void formed in the porous coordinatively unsaturated metal complex by connecting a number of "metal complex units" one another by the "connecting metals". As is obvious from FIG. 4, plural organic ligands define a rectangular or a substantially rectangular hollow in plan view. Placing these organic ligands one over another defines a void. In this specification, a tunnel-like void which extends in one direction is referred to as a "one-dimensional" void, a void which extends in two different directions orthogonal to each other is referred to as a "two-dimensional" void, and a void which extends in three different directions orthogonal to one another is referred to as a "three-dimensional" void. In this invention, a porous metal complex having one-, two-, or three-dimensional voids can be easily formed by designing the structure of the metal complex unit and the connecting metal.

"Porous" in this invention means that the metal complex has at least one void. Preferably, however, if more than one void is formed in the metal complex, these voids may be one-dimensional or three-dimensional.

The void formed in the porous coordinatively unsaturated metal complex of this invention has a size of 10 Å or larger. It is preferable that a spherical component having a diameter of 10 Å or larger is allowed to be incorporated in the void. The cross sectional configuration of the void is not specifically limited. In the case, however, that the void has a rectangular or a substantially rectangular shape in cross section, the shortest side of the void is 10 Å or longer. It is preferable that substantially all the void of "porous coordinatively unsaturated metal complex" of this invention has a size of 10 Å or larger.

Heretofore, a layered complex has been known in which a substrate comprised of a small molecule such as methane gas is incorporated. The conventional layered complex, however, fails to serve as a porous metal complex of practical use capable of incorporating a general compound as a substrate and having voids of a sufficient size to exhibit substrate selectivity. Therefore, the porous metal complex of this invention is obviously differentiated from the prior art layered complex in its technical significance.

The "organic ligand" in this invention may be a cyclic organic ligand in which two or more of the compound of formula (I) or (III) are connected each other or one another by way of α groups of organic ligands adjacent to each other wherein a hydrogen atom on the α group is substituted by a $C_1$–$C_6$alkylene group or —(C=O)—($C_1$–$C_6$alkylene)-(C=O)— group. Such a cyclic organic ligand may be a compound represented by the following formula:

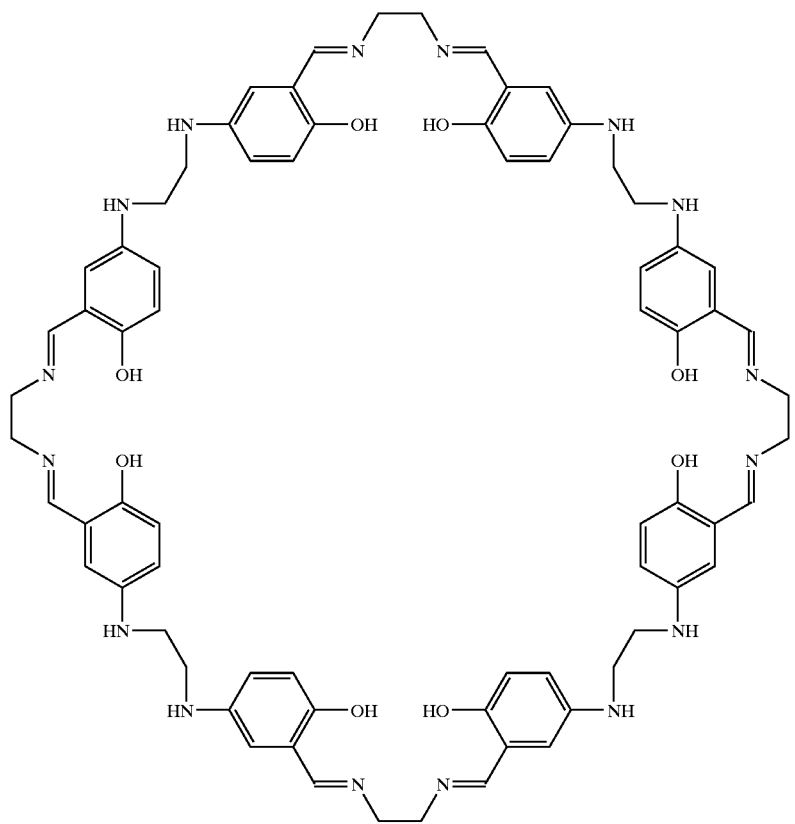

The "organic ligand" in this invention may be a compound of formula (IV), which is a derivative of the compound of formula (I).

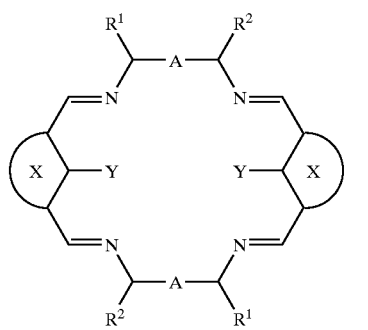
(IV)

[wherein, A, X, Y, $R^1$ and $R^2$ are as defined above.]

The "organic ligand" in this invention may be a compound of formula (V) or formula (VI), in addition to the compounds of formulae (I), (III).

The compound of formula (V) has the following structure.

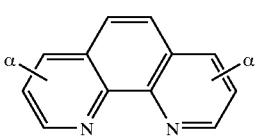
($V^1$)

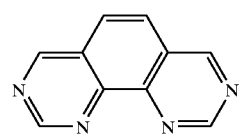
($V^2$)

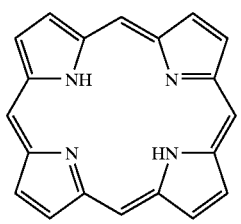
($V^3$)

[wherein α is as defined above, and the compound of formula ($V^3$) contains 1 to 4 α groups and may be substituted by 1 to 4 β groups.]

The compound of formula (VI) has the following structure.

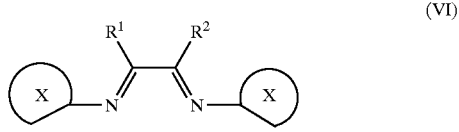

(VI)

[wherein X, R¹ and R² are as defined above.]

In the definition of each groups of the above formulae, "monocyclic or a condensed aromatic hydrocarbon group" means monovalent or divalent monocyclic or condensed aromatic hydrocarbon group, "C6–C12 monocyclic or a condensed aromatic hydrocarbon group" may include phenyl (phenylene), pentalenyl (pentalenylene), indenyl (indenylene), naphthyl (naphthylene), and azulenyl (azulenylene), "C6–C22 monocyclic or a condensed aromatic hydrocarbon group" may include, in addition of these C6–C12 aromatic hydrocarbon group, heptalenyl (heptalenylene), biphenylenyl (biphenylenylene), phenalenyl (phenalenylene), phenanthrenyl (phenanthrenylene), anthracenyl (anthracenylene), pyrenyl (pyrenylene), dibenzophenanthrenyl (dibenzophenanthrenylene), and 9,10-dihydrodibenzophenanthrenyl (9,10-dihydrodibenzophenanthrenylene). In the case that "X" represents $C_6$–$C_{10}$ monocyclic or a condensed aromatic hydrocarbon group, it is preferably phenylene or naphthylene, more preferably phenylene. In the case that the partial structure integrally comprised of $R^1$, $R^2$, carbon atoms respectively adjacent thereto, and "A" or $R^{1'}$, $R^{2'}$, carbon atoms respectively adjacent thereto, and "A" represents a $C_6$–$C_{22}$ monocyclic or a condensed aromatic hydrocarbon group, the structure represent the 1,2-substituted aromatic hydrocarbon mentioned above, preferably $C_6$–$C_{10}$ monocyclic or a condensed aromatic hydrocarbon group, more preferably 1,2-phenylene, 1,2- or 2,3-naphthylene, most preferably 1,2-phenylene.

The "nitrogen-containing heteroaryl group" means monocyclic or condensed aromatic heterocyclic group containing 1 to 4 nitrogen atom as hetero atom, may include 5-membered monocyclic nitrogen-containing heteroaryl such as pyrrolyl, pyrazolyl, imidazolyl, oxazolyl, isoxazolyl, thiazolyl, isothiazolyl, 1,2,3-oxadiazolyl, thiadiazolyl, triazolyl; 6-membered monocyclic nitrogen-containing heteroaryl such as pyridyl, pyridazinyl, pyrimidinyl, pyrazinyl; 9-membered condensed nitrogen-containing heteroaryl such as indolizinyl, isoindolyl, indolyl, benzooxazolyl, benzothiazolyl; 10-membered condensed nitrogen-containing heteroaryl such as isoquinolinyl, quinolinyl. In the case that "X" or "α" is nitrogen-containing heteroaryl group, it is preferably 5- or 6-membered monocyclic nitrogen-containing heteroaryl, more preferably 6-membered monocyclic nitrogen-containing heteroaryl, most preferably pyridyl.

The "alkyl group" means a straight or branched chain aliphatic hydrocarbon, may include C1–C6alkyl such as methyl, ethyl, propyl, isopropyl, butyl, isobutyl, s-butyl, tert-butyl, pentyl, s-pentyl, isoamyl, 2-methylbutyl, neopentyl, 1-ethylpropyl, hexyl, 4-methylpentyl (isohexyl), 3-methylpentyl, 2-methylpentyl, 1-methylpentyl (s-hexyl), 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl. In the case that $R^1$, $R^2$, $R^{1'}$, $R^{2'}$ or "β" is alkyl group, it is preferably C1–C4alkyl group, more preferably C1–C2alkyl group, most preferably methyl group.

The "di(C1–C6alkyl)amino group" means amino group which is substituted by two C1–C6alkyl groups mentioned above, may include dimethylamino, dietylamino, diisopropylamino, ethylmethylamino. In the case that "Y" or "Y'" is di($C_1$–$C_6$alkyl)amino group, it is preferably di($C_1$–$C_4$alkyl)amino group, more preferably dimethylamino group.

The "di($C_1$–$C_6$alkyl)phosphino group" means phosphorus atom which is substituted by two C1–C6alkyl group mentioned above, may include dimethylphosphino, dietylphosphino, diisopropylphosphino, di-t-butylphosphino. In the case that "Y" or "Y'" is di($C_1$–$C_6$alkyl)phosphino group, it is preferably di($C_1$–$C_4$alkyl)phosphino group, more preferably di-(t-butyl)phosphino group.

The "diarylphosphino group" means phosphorus atom which is substituted by two aryl group mentioned above, may include diphenylphosphino, dinaphthylphosphino. In the case that "Y" or "Y'" is diarylphosphino group, it is preferably diphenylphosphino group.

The "alkenyl group" means a straight or branched chain aliphatic hydrocarbon having more than one double bond between two carbon atom, may include C2–C6alkenyl such as ethenyl, propenyl, methylpropenyl, ethylpropenyl, butenyl, methylbutenyl, ethylbutenyl, pentenyl, methylpentenyl, hexenyl. In case that $R^1$, $R^2$, $R^{1'}$ or $R^{2'}$ is C2–C6alkenyl, it is preferably (C2–C4)alkenyl, more preferably ethenyl. But in case that "A" is double bond, the bond between the carbon atom adjacent to "A" and the substituting carbon atom in $R^1$, $R^2$, $R^{1'}$ or $R^{2'}$ is not double bond.

The "alkoxy group" means a straight or branched chain aliphatic hydrocarbon oxy group, may include C1–C6alkoxy such as methoxy, ethoxy, propoxy, isopropoxy, butoxy, isobutoxy, s-butoxy, t-butoxy, pentyloxy, isopentyloxy, 2-methylbutoxy, neopentyloxy, 1-ethylpropoxy, hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy. In case that $R^1$, $R^2$, $R^{1'}$, $R^{2'}$ or β is C1–C6alkoxy, it is preferably (C1–C4)alkoxyl, more preferably (C1–C2)alkoxyl, most preferably methoxy.

The "halogen atom" may include a fluorine atom, a chlorine atom, a bromine atom and an iodine atom. In case that $R^1$, $R^2$, $R^{1'}$, $R^{2'}$ or β is halogen atom, it is preferably fluorine atom, a chlorine atom or a bromine atom, more preferably fluorine atom.

The "cyclic hydrocarbon group" means cyclic saturated hydrocarbon group, may include C3–C6 cyclic hydrocarbon group, such as cyclopropyl, cyclobutyl, cyclopentyl and cyclohexyl. In case that the partial structure integrally comprised of $R^1$, $R^2$, carbon atoms respectively adjacent thereto, and "A" or comprised of $R^{1'}$, $R^{2'}$, carbon atoms respectively adjacent thereto, and "A" is C3–C6 cyclic hydrocarbon group, it is preferably is C5–C6 cyclic hydrocarbon group, more preferably 1,2-cyclohexyl.

The "alkylene group" means a straight or branched chain saturated aliphatic hydrocarbon divalent group, may include C1–C6alkylene group such as methylene, ethylene, methylmethylene, trimethylene, methylethylene, dimethylmethylene, tetramethylene, methylpropylene, pentamethylene, dimethylpropylene, hexamethylene, isopropylpropylene. C1–C6Alkylene group or C1–C6alkylene group included in —(C=O)—(C₁–C₆alkylene)-(C=O)— group is preferably C1–C4 alkylene, more preferably C1–C2alkylene.

In the case where A represents a C—C single bond in the compound of formula (I), a hydrogen atom is bound to the carbon atom contiguous to A. In the case where $R^1$, $R^2$ each represents a hydrogen atom, two hydrogen atoms are bound to the carbon atom contiguous to A, and in the case where $R^1$, $R^2$ each represents a 1–$C_2$–$C_6$alkenyl group, no hydrogen atom is bound. Further, in the case where A is absent, the carbon atom contiguous to A becomes methylene (in the case where $R^1$, $R^2$ each represents a hydrogen atom, the carbon becomes methyl, and in the case where $R^1$, $R^2$ each represents a 1–$C_2$–$C_6$alkenyl group, the carbon atom becomes methine).

$R^1$ and $R^2$ or $R^{1'}$ and $R^{2'}$ are respectively identical to or different from each other in the compounds of formulae (I) through (IV). However, in the case where the organic ligand is symmetrical, it is easy to regularly array the coordinatively unsaturated metals in the metal complex. In view of this, it is preferable that $R^1$, $R^2$, and $R^{1'}$, $R^{2'}$ are respectively identical to each other.

For the same reason as mentioned above, it is preferable that the substituting positions of the α groups in the compounds of formulae (I) through (IV) are symmetrical to each other with respect to an axis or a plane or symmetrical to each other with respect to a certain point in the compound, as shown in the following formula. More preferably, the substituting positions are symmetrical to each other in the former meaning.

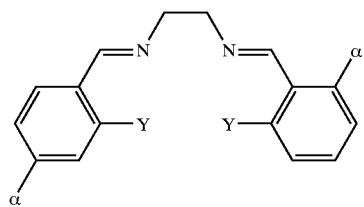

The α group has an action of connecting organic ligands adjacent to each other in the metal complex of this invention by being coordinatively bound to a corresponding connecting metal. In view of this, it is preferable that these a groups may be arranged symmetrical to each other in the organic ligands in order to allow the organic ligands and resultantly coordinatively unsaturated metals to be arrayed regularly. Further, in the case where a plurality of α groups are used for each one of the organic ligands, the α groups in one organic ligand may be identical to or different from each other, it is preferably identical to each other. And preferably; the substituting positions of the α groups are symmetrical to each other with respect to an axis or a plane, or with respect to a point. More preferably, the substituting positions are symmetrical to each other in the latter meaning. Preferably, the number of the a groups substituting on one aromatic hydrocarbon group is one or two, and more preferably one.

For the same reason as mentioned above, in the case where there exists a plurality of β groups in each one of the compounds of formulae (I) through (IV) and (VI), the β groups may be identical to or different from each other. Preferably, the number of the β groups is zero, one, or two.

In the case where the compound of this invention has an acidic group such as a carboxyl group, such a compound may include a salt thereof. This is because a salt may be usable in producing the metal complex of this invention. Such salts may include such as alkali metal salts (e.g., sodium salt, potassium salt, lithium salt.), alkaline earth metal salts (e.g., calcium salt, magnesium salt.), a metal salts (e.g. ferrous salt, zinc salt, copper salt, nickel salt, cobalt salt.), inorganic salt such as an ammonium salt, organic amine salt (e.g. t-octylamine salt, dibenzylamine salt, morpholine salt, glucosamine salt, phenylglycinealkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-N-phenetylamine salt, piperazine salt, tetramethylammonium salt, tris(hydroxymethyl)aminomethane salt.), or the like.

There is a case that the compound of this invention has a basic group such as a nitrogen-containing heteroaryl group. In such a case, similar to the above case in which the compound has an acidic group, the compound may include a salt thereof. Some of the examples of the salts are: halogenated hydrogen salt such as hydrofluoride, hydrochloride, hydrobromide, hydroiodide; inorganic acid salt such as nitrate, perchloride, sulfate, phosphate; loweralkane sulfonate such as methanesulfonate, trifluoromethanesulfonate, etnanesulfonate; arylsulfonate such as benzenesulfonate, p-toluenesulfonate; amino acid salt such as ornithine salt, glutamic acid salt; carboxy acid salt such as fumarate, succinate, citrate, tartarate, oxalate, maleate.

Further, there is a case that the compound of this invention becomes a solvate (hydrate) by absorbing or adsorbing a water component or a solvent in the course of a synthesizing process or in a storage of a synthesized product. The compound of this invention may include such a solvate (hydrate). Further, there is a case that various isomers or tautomers are yielded as the compound of this invention. Such a case is embraced in this invention.

Hereinafter, what is disclosed in the above regarding this invention is described in further detail.

First, to summarize this invention, the primary feature of the porous coordinatively unsaturated metal complex of the present invention resides in that: the metal complex is porous because of connection of a number of metal complex units by connecting metals; and that the metal complex can selectively incorporate a substrate molecule due to its porosity. Further, this invention is advantageous in selectively reacting the incorporated substrate molecule as a reactive substrate owing to the action of the metal in a coordinatively unsaturated state as a component substance or in securely holding the substrate molecule in a void.

The size of the void in the porous coordinatively unsaturated metal complex of this invention is determined depending on the metal complex unit and the connecting metal constituting the metal complex. Accordingly, the metal complex unit and the connecting metal can be designed in such a manner that the distance between metals or metal ions in a coordinatively unsaturated state, orientation of the metal (metal ion), and size of the void may be set depending on a substrate molecule to be incorporated. In other words, whereas the conventional porous metal complex, even of a practical use, limitedly incorporates low-molecular weight compounds such as water and methane gas, the porous metal complex of this invention is capable of incorporating general compounds as substrates because of voids having a sufficiently large size.

There is a case that unavoidable impurities such as solvents and molecules in the air may be intruded in a metal complex in the course of production or in storage of the metal complex. This invention embraces such a case that unavoidable impurities are intruded, as far as the resultant metal complex can exhibit the aforementioned actions and effects. Generally, even if the impurities are intruded in, it is conceived that the structure of a metal complex is not brought to such a disordered state that voids as defined in this invention are not formed in the metal complex, as far as the metal complex unit comprised of the aforementioned coordinatively unsaturated metal and the aforementioned organic ligand, and the aforementioned connecting metal are used as component substances constituting the metal complex of this invention.

The "porous coordinatively unsaturated metal complex" of this invention is producible according to the following process A.

(Process A)

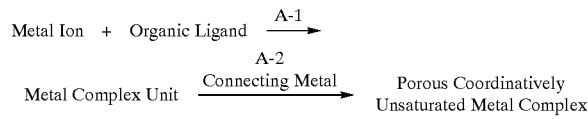

The process A is a process for producing the porous coordinatively unsaturated metal complex of this invention by using metals or metal ions (first metals), organic ligands, and connecting metals (second metals). Generally, a porous coordinatively unsaturated metal complex is produced by mixing a solution containing organic ligands and a solution containing metal salts having plural coordination bondability to prepare metal complex units and by adding a compound as a raw material for connecting metals to a solution containing the metal complex units.

The process A comprises a step A-1. The step A-1 is a step of preparing metal complex units. Specifically, in the step A-1, a solution containing organic ligands and a solution containing metal salts having plural coordination bondability are mixed together to synthesize a complex (metal complex units of this invention) in which each metal is supported to a corresponding organic ligand in a coordinatively unsaturated state. In this process, it may be possible to apply heat or pressure in the reaction system to accelerate formation of the metal complex units.

The solvent used as a solution (organic-ligand-solution) for dissolving organic ligands and a solution (metal-salt-solution) for dissolving metal salts is not specifically limited, as far as the solvent can sufficiently dissolve these raw material compounds and may not adversely affect the reaction. Examples of the solvent include: amides such as dimethylformamide, dimethylacetoamide; ethers such as methylethylether, diethylether, tetrahydrofuran; $C_3$–$C_6$glycolether such as methyl cellosolve, ethyl cellosolve, butyl cellosolve; water-soluble aromatic organic solvents such as pyridine; alcohols such as methanol, ethanol, n-propanol, 2-propanol, n-butanol, hexanol, cyclohexanol; water: ketones such as acetone, methylethylketone, methyl isopropylketone; and a solvent in which two or more kinds of these compounds are mixed. The solvent used as the organic-ligand-solution and the solvent used as the metal-salt-solution may be identical to or different from each other. Preferably, the solutions are identical to each other.

Although the reaction can be carried out at room temperature, it may be preferable to heat the reaction system to dissolve the raw material compounds well or to accelerate formation of the metal complex units. A preferable reaction temperature is from 10 to 200° C., and more preferably from 20 to 100° C.

The pressure to be applied to the reaction system is not specifically limited. For instance, efficient synthesis is executable by carrying out the reaction at a pressure of from 0.1 to 1 MPa.

The time for reaction is not specifically limited. There is a case that adding the solution dropwise sufficiently slowly enables to eliminate or shorten a reaction time that is required in a post-process. In the case where it is conceived that the metals are not sufficiently bound to the organic ligands in a coordinatively unsaturated state, the reaction system may preferably stand still from one night to several days.

After the reaction is completed, precipitate as a sub-product is filtrated, and water or lower alcohol is added to the filtrate. As a result, metal complex units as a target compound are precipitated. The thus obtained metal complex units have sufficiently high purity. However, the metal complex units can be purified by a known purifying process such as re-crystallization.

It is possible that merely metals or metal ions in the metal complex units are substituted. Namely, substitution of coordinatively unsaturated metals can be carried out by dissolving the metal complex units in a solvent and by adding a desired metal-salt solution dropwise. The solvent used in the reaction, the reaction temperature, the reaction time, the post-process, and other conditions may be the same as those employed in the aforementioned step A-1.

Further, it is possible to prepare metal complex units in each of which two or more kinds of coordinatively unsaturated metals are supported to an organic ligand as an overall unit by adding a metal-salt-solution containing two or more kinds of metals dropwise.

A step A-2 is a step for producing the porous coordinatively unsaturated metal complex of this invention by connecting the metal complex units obtained in the step A-1 by connecting metals.

Generally, the step A-2 is carried out in such a manner that metal complex units are dissolved in a solvent, and that a salt of connecting metals is added to the metal complex units. In the step A-2, a certain pressure may be applied to accelerate formation of the complex.

The solvent used in the step A-2 is not specifically limited as far as it does not interfere formation of the complex. Examples of the solvent include amides such as dimethylformamide, dimethylacetoamide; ethers such as methylethylether, diethylether, tetrahydrofuran; $C_3$–$C_6$glycolether such as methyl cellosolve, ethyl cellosolve, butyl cellosolve; water-soluble aromatic organic solvents such as pyridine; alcohols such as methanol, ethanol, n-propanol, 2-propanol, n-butanol, hexanol, cyclohexanol; water: ketones such as acetone, methylethylketone, methyl isopropylketone; and a solvent in which two or more kinds of these compounds are mixed.

Although the reaction can be carried out at room temperature, it may be preferable to heat the reaction system to such an extent as to dissolve the raw material compounds such as metal complex units and connecting metals well or to accelerate formation of the complex. A preferable reaction temperature is from 10 to 200° C., and more preferably from 20 to 150° C.

The pressure to be applied to the reaction system is not specifically limited. For instance, efficient synthesis is executable by carrying out the reaction at a pressure of from 0.1 to 1 MPa.

The reaction time is not specifically limited. Preferably, the reaction system may stand still from several hours to several days.

A target porous coordinatively unsaturated metal complex is insoluble in water and/or a water-soluble solvent. Accordingly, the metal complex may give rise to crystals. In view of this, it is preferable that the target compound is filtrated, washed with a waterborne solvent, and dried after the reaction is completed.

It is conceived that the porous coordinatively unsaturated metal complex of this invention is provided with versatile catalytic functions by coordinatively binding two or more of transition metals to an organic ligand.

The porous coordinatively unsaturated metal complex of this invention is configured such that a coordinatively unsaturated metal (M) is, for example, coordinatively bound in the following manner.

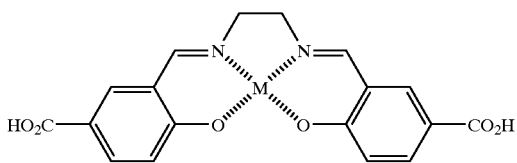

It should be appreciated, however, that in the case where A is absent in the compound of formula (I), there is a possibility that the metal (M) is coordinatively bound in the following manner.

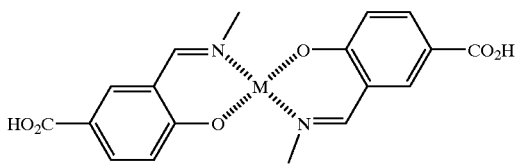

It is, however, preferable that the metal complex units have a predetermined fixed coordination mode and conformation to array the coordinatively unsaturated metals regularly. In view of this, it is preferable that A is present, namely, A is a C—C single bond or a double bond in the compound of formula (I). Furthermore preferably, free rotation between C—C at the position of A may be avoided.

The compound of formula (I), which is an organic ligand, is producible according to, e.g., a process B.

(Process B)

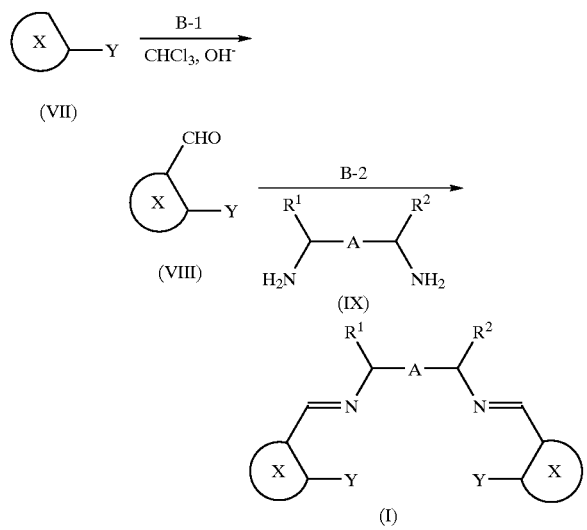

[wherein, A, X, Y, R$^1$ and R$^2$ are as defined above.]

The process B is a process for producing the compound of formula (I) that is an organic ligand.

The process B comprises a step B-1. The step B-1 is a step for producing the compound of formula (VIII) from the compound of formula (VII). Specifically, since the compound of formula (VII) exhibits a property inherent to an aromatic group, a formyl group can be introduced to the carbon atom adjacent to the hydroxyl group by Reimer-Tiemann reaction.

The reaction is conducted by adding chloroform in an alkali hydroxide solution containing the compound of formula (VII).

Since the chemical formula (VII) is relatively simple, it is possible to purchase a commercially available compound, or to synthesize the compound of formula (VII) from the commercially available compound according to a known process.

The alkali hydroxide used in the reaction is not specifically limited. Sodium hydroxide and potassium hydroxide are examples of the alkali hydroxide.

The solvent used in the reaction is not specifically limited as far as it can dissolve a reactive substrate and does not interfere the reaction. For example, water, and a solvent in which water and a water-soluble organic solvent such as alcohol are mixed are exemplified.

It is preferable that the reaction is carried out in an appropriately heated condition. A preferable reaction temperature is from room temperature to 100° C.

The reaction time differs depending on the reaction temperature and the like. Normally, the reaction time is from 1 to 8 hours.

After the reaction is completed, extraction, drying, and distilling off of the organic solvent in vacuo are conducted according to a known process to yield a target compound of formula (VIII). The target compound can then be purified according to re-crystallization, chromatography, and the like.

A step B-2 is a step for producing the compound of formula (I) from the compound of formula (VIII) and a compound of formula (IX). Specifically, the target compound of formula (I) can be synthesized by forming a Schiff base with use of a formyl group in the compound of formula (VIII) and the compound of formula (IX) which is an amine compound.

The reaction is accomplished by adding a solution containing the compound of formula (IX) to a solution containing the compound of formula (VIII).

The organic solvent used in the reaction is not specifically limited as far as it can dissolve the compounds of formulae (VIII), (IX) and does not interfere the reaction. The organic solvent includes: alcohols such as methanol and ethanol; ethers such as diethylether and tetrahydrofuran; amides such as dimethylformamide and diethylacetoamide; and a solvent in which two or more kinds of these compounds are mixed.

The reaction temperature differs depending on the raw material compound to be used in the reaction, the solvent, and the like. Normally, the reaction temperature is from room temperature to 200° C., and preferably, from room temperature to 100° C.

The reaction time differs depending on the raw material compound to be used in the reaction, the solvent, and the like. The reaction is substantially accomplished by adding the solution containing the compound of formula (IX) gradually dropwise. It is, however, preferable to stand the solution still for several hours after the addition.

After the reaction is completed, if the target compound of formula of formula (I) is precipitated, the solution is filtrated without any other procedure. If, however, the target compound is not precipitated, it may be preferable to distill off the solvent in vacuo. Further, the obtained target product can be purified by re-crystallization, chromatography, and the like.

The compound of formula (V¹), which is an organic ligand, can be obtained by using a commercially available compound or by introducing 1,10-phenanthroline to the a group or by performing a substitution reaction of a 1,10-phenanthroline derivative according to a known process.

The compound of formula (VI) which is an organic ligand is producible according to, e.g., the following process C.

(Process C)

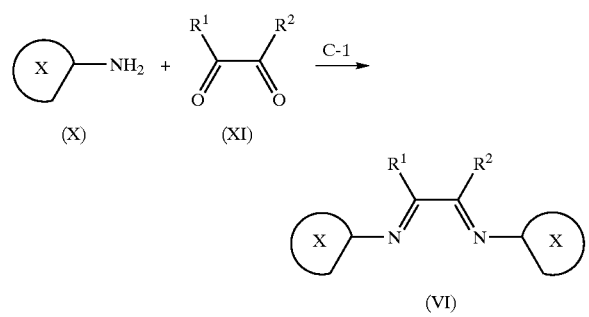

[wherein X, R¹ and R² are as defined above.]

The process C is a process for producing the compound of formula (VI) which is an organic ligand.

The process C comprises a step C-1. The step C-1 is a step for producing the compound of formula (VI) from compounds of formulae (X) and (XI). Specifically, the target compound of formula (VI) can be synthesized by forming a Schiff base with use of a amino group in the compound of formula (X) and carbonyl groups in the compound of formula (XI).

The reaction is accomplished by adding a solution containing the compound of formula (XI) to a solution containing the compound of formula (X) dropwise. It is possible to add an acid such as a formic acid when need arises to do so.

The organic solvent used in the reaction is not specifically limited as far as it can dissolve the compounds of formulae (X), (XI) and does not interfere the reaction. The organic solvent includes: alcohols such as methanol and ethanol; ethers such as diethylether and tetrahydrofuran; amides such as dimethylformamide and dimethylacetoamide; and a solvent in which two or more kinds of these compounds are mixed.

The reaction temperature differs depending on the raw material compound to be used in the reaction, the solvent, and the like. Normally, the reaction temperature is from room temperature to 100° C., and preferably, room temperature.

The reaction time differs depending on the raw material compound to be used in the reaction, the solvent, and the like. The reaction is substantially accomplished by adding the solution containing the compound of formula (XI) gradually dropwise. It is, however, preferable to stand the solution still for several hours after the addition.

After the reaction is completed, if the target compound of formula (VI) is precipitated, the solution is filtrated without any other procedure. If, however, the target compound is not precipitated, it may be preferable to distill off the solvent in vacuo. Further, the obtained target product can be purified by re-crystallization, chromatography, and the like.

Figure 7:
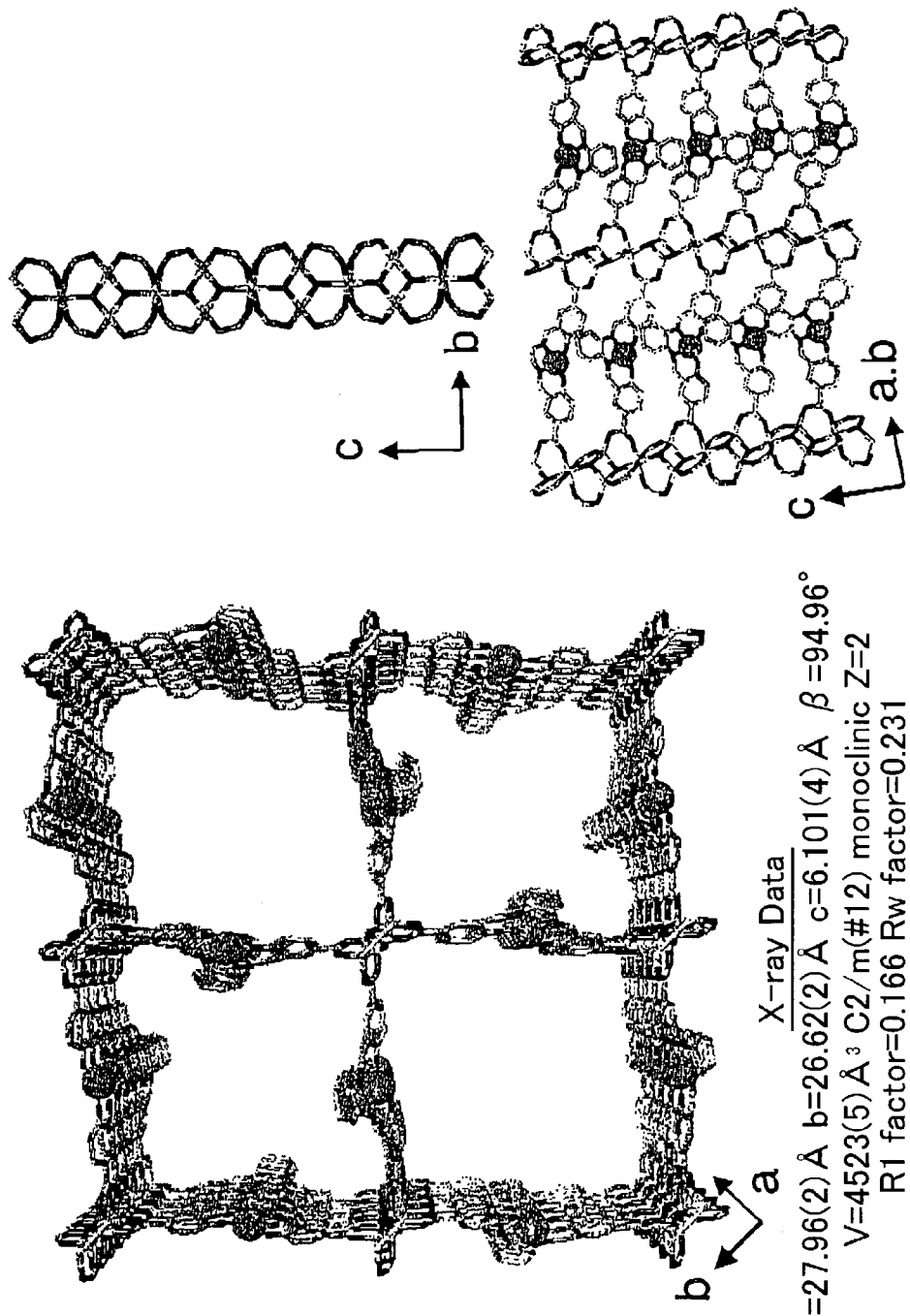
FIG. 7 is an illustration showing a result of X-ray crystallographic analysis of the porous coordinatively unsaturated metal complex of this invention.

Using the aforementioned organic ligand is advantageous in forming a porous coordinatively unsaturated metal complex in which, as shown in FIG. 7, a rectangular or a substantially rectangular hollow is defined by four organic ligands connected to each other, a number of the hollows are arrayed in a substantially honeycomb manner to form a network structure and the network structures are placed one over another to form a structure in which a number of voids each having a certain size are formed. Specifically, since the length of a side of a polyhedron defining a void is determined depending on the structure of the metal complex unit and the connecting metal to be used, a metal complex formed with voids of desired dimensions can be obtained by designing the structure of the organic ligand. For instance, in the case where a reactive substrate is a small molecule such as oxygen and methane gas, there is no necessity of considering the dimensions of the void. However, in the case where a reactive substrate is a relatively large molecule, reaction selectivity is obtainable by using an organic ligand suitable for the purpose. Preferably, the size of the void is 10 Å or more, more preferably, 11 Å or more, 12 Å or more, 13 Å or more, and optimally, 14 Å or more. As far as the metal complex has voids of the aforementioned size, starting materials used in most of organochemical reactions can be incorporated in the voids as substrates.

If the porous coordinatively unsaturated metal complex of this invention is solid at room temperature, and exhibits water insolubility or hardly-soluble property in water, the porous metal complex can be easily precipitated by adding water or the like to a synthesizing system, and re-crystallized, which is convenient in the aspect of production. Furthermore, the porous metal complex of this invention is free from a drawback that the complex becomes unstable due to adsorption of water in the environment during its storage. Generally, "water-insoluble" means that water of 10,000 g or more is required to dissolve a sample of 1 g, and "hardly-soluble in water" means that water of 1,000 to less than 10,000 g is required to dissolve a sample of 1 g. As far as the purpose of this invention is attainable, the porous coordinatively unsaturated metal complex of this invention may have solubility higher than these values.

The porous coordinatively unsaturated metal complex of this invention is capable of releasing a molecule that has been selectively incorporated. For instance, it is conceived that a molecule that has been incorporated and held in a metal complex may be released out of the metal complex by applying heat or the like, and that a substrate that has been subjected to a catalytic activity of the metal complex may be released out of the metal complex as a target product of reaction owing to low affinity between the product of reaction and the coordinatively unsaturated metal.

Hereinafter, this invention is described in further detail with reference to Examples. It should be appreciated that the scope of this invention is not limited to the following Examples.

EXAMPLE 1

Example 1-1

Preparation of 3-formyl-4-hydroxybenzoic acid

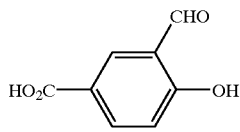

In a reactor 20 g of 4-hydroxybenzoic acid and 36 g of sodium hydroxide were loaded, and nitrogen replacement was carried out for 10 minutes at room temperature. To the mixture 100 ml of water was added, and the mixture was heated at 70° C. while being stirred. Next, 20 ml of chloroform was added dropwise through a funnel, and precipitate of brown color was obtained.

To the mixture 300 ml of water was added, and a homogeneous solution was obtained. Then, hydrochloric acid was added until the solution exhibited acidity. As a result, white colored precipitate was obtained. The white precipitate was extracted with diethylether, and the solvent was evaporated. As a result of concentration, brownish white solid was obtained.

Example 1-2

Preparation of Organic Ligand of Salen Type

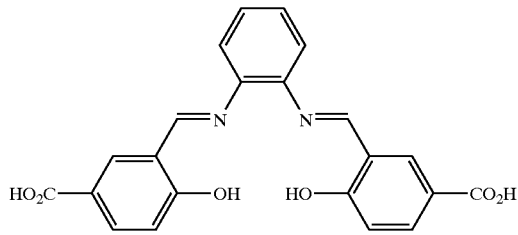

In 100 ml of methanol 1.0839 g of 3-formyl-4-hydroxy benzoic acid obtained by Example 1-1 was dissolved, and to the solution a methanol solution containing 0.3525 g of phenylenediamine was gradually added dropwise at room temperature. As a result of addition, orange colored precipitate was yielded.

The solution was filtered after letting it stand still for one hour. As a result of filtration, 1.1105 g of orange colored solid was obtained.

Figure 5:
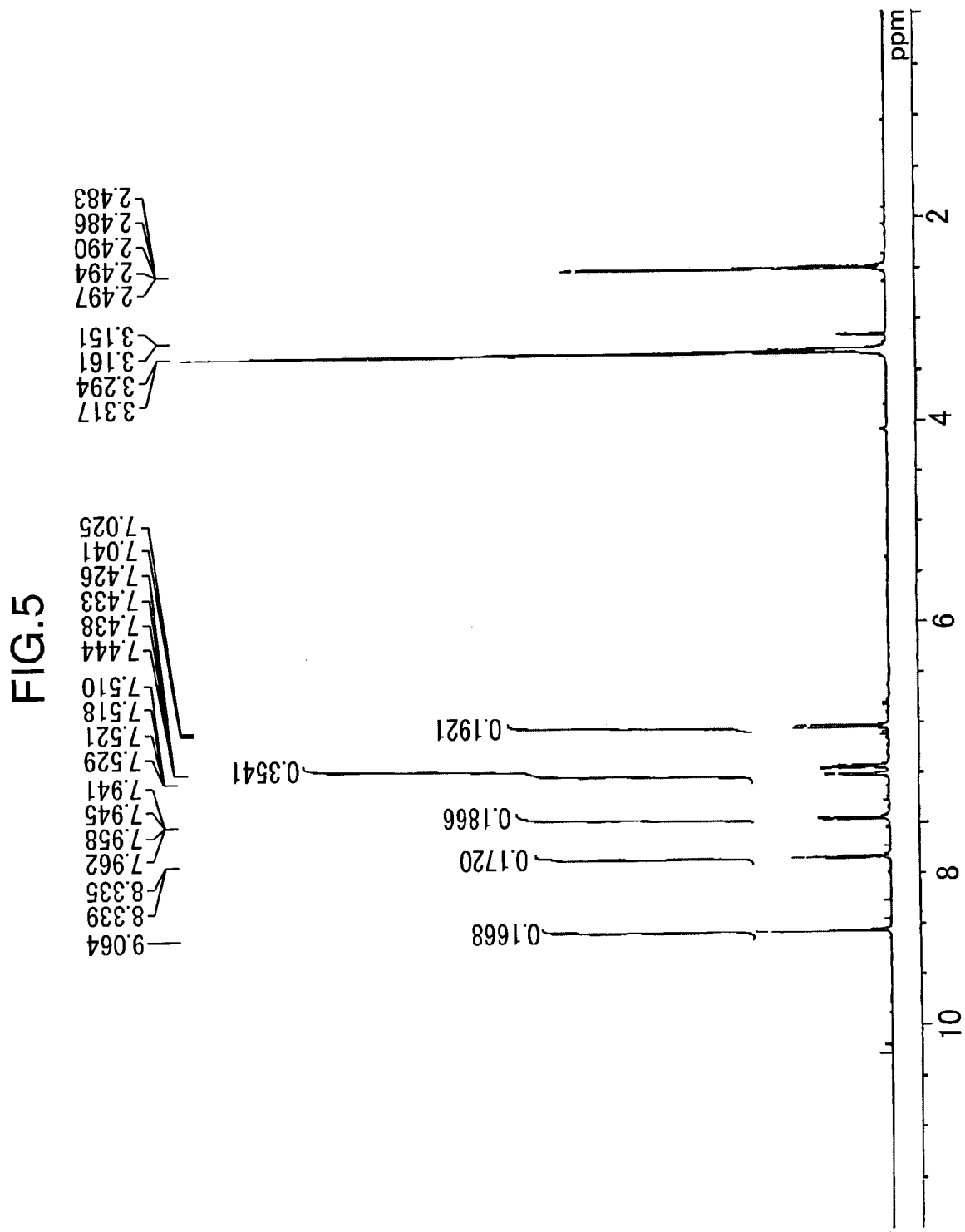
FIG. 5 is a chart showing nuclear magnetic resonance (NMR) of a salen-type organic ligand (Example 1-2) of this invention.
Figure 6:
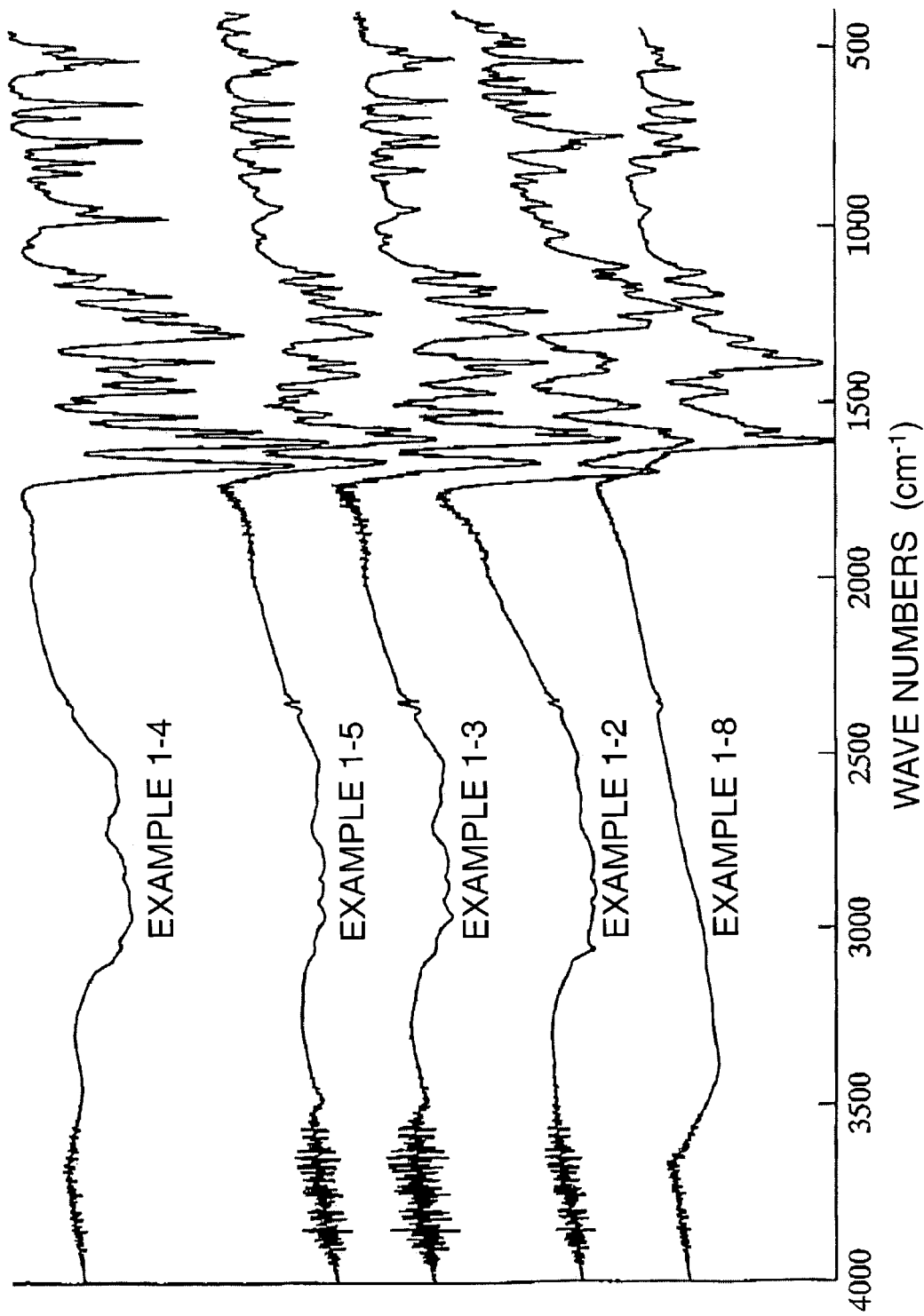
FIG. 6 is a chart showing results of infrared radiation (IR) with respect to products of reactions obtained in Examples 1-2, 1-3, 1-4, 1-5, and 1-8 of this invention.

FIG. 5 shows a result of NMR analysis of the product obtained in Example 1-2 measured in dimethylsulfoxide-$d_6$. FIG. 6 shows a result of IR measurement of the product obtained in Example 1-2.

Example 1-3

Preparation of Metal Complex Unit in which Copper is Coordinatively Bounded

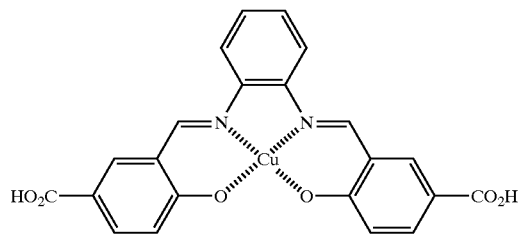

In dimethylformamide 0.2022 g of the salen-type organic ligand obtained by Example 1-2 was dissolved, and a dimethylformamide solution containing 0.0998 g of copper (II) acetate was added dropwise at room temperature. As a result of addition, deep-green precipitate was yielded. 150 ml of Dimethylformamide was used in total.

The precipitate was removed by filtration, and methanol was added to the resultant filtrate. As a result of adding methanol, 0.15 g of brown powder was obtained.

IR measurement and mass spectrum measurement were performed with respect to the resultant product. IR analysis data of Example 1-3 is shown in FIG. 6. Mass spectrum measurement showed that the peak of molecular ions of the reaction product in Example 1-3 was 465.

Example 1-4

Preparation of Metal Complex Unit in which Vanadium is Coordinatively Bounded

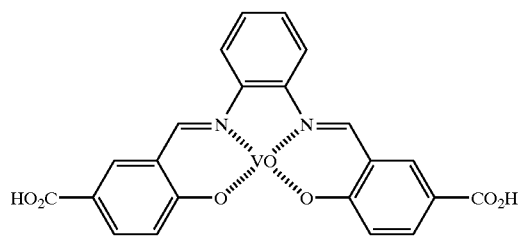

An experiment was conducted in the same manner as Example 1-3 except that 0.1449 g of vanadium sulfate ($VOSO_4$) was used in place of copper acetate.

IR measurement and mass spectrum measurement were performed with respect to the resultant product. IR analysis data of Example 1-4 is shown in FIG. 6. Mass spectrum measurement showed that the peak of molecular ion of the reaction product in Example 1-4 was 469. The result of mass spectrum measurement reveals that the component coordinatively bound to the organic ligand is VO.

Example 1-5

Preparation of Metal Complex Unit in which Nickel is Coordinatively Bounded

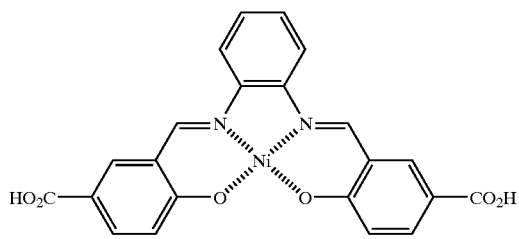

An experiment was conducted in the same manner as Example 1-3 except that 0.100 g of nickel acetate was used in place of copper acetate. As a result, metal complex units in which nickel was coordinatively bound to organic ligand was prepared, and IR measurement was conducted. The result of IR measurement is shown in FIG. 6.

Example 1-6

Preparation of Organic Ligand of Salen Type

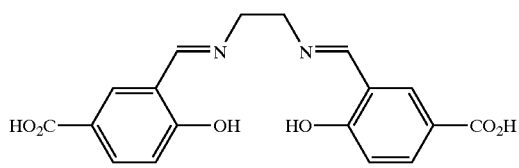

An experiment was conducted in the same manner as Example 1-2 except that 0.1959 g of ethylenediamine was used in place of phenylenediamine, and the organic ligand having the above structure was obtained.

Mass spectrum measurement result reveals that the peak of molecular ion of the resultant product in Example 1-6 was 355 in terms of (M−H)$^-$.

Example 1-7

Preparation of Organic Ligand of Salen Type

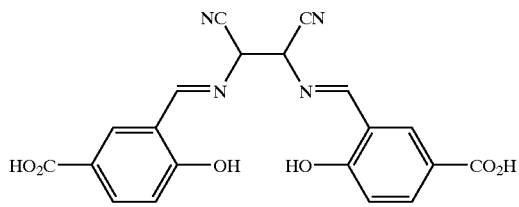

An experiment was conducted in the same manner as Example 1-2 except that 1,2-dicyanoethylenediamine was used in place of phenylenediamine, and the organic ligand having the above structure was obtained.

Mass spectrum measurement result reveals that the peak of molecular ions was 404 with two hydrogen atoms being dissociated between C—C bond to which a cyano group was bound.

Example 1-8

Production of the Porous Coordinatively Unsaturated Metal Complex

In 50 ml of a dimethylformamide 0.101 g (0.25 mmol) of the metal complex units obtained by Example 1-3 in which copper (II) has been coordinatively bound was dissolved. After stirring the solution at room temperature for about 5 hours, 3.0 mmol of pyridine was added. Then, 50 ml of a dimethylformamide solution containing 0.25 mmol of zinc nitrate (product of Wako Pure Chemicals Industries, Ltd.) was added. After adding 20 ml of water further and letting the solution stand still at 65° C., a target product, which was single crystal, was yielded.

IR measurement (see FIG. 6), X-ray crystallographic analysis (FIG. 7), powder X-ray diffractometry (see FIG. 8), and thermogravimetry (see FIG. 9) were conducted with respect to the resultant single crystalline structure.

In FIG. 7, symbols "a", "b" and "c" denote lengths of the resultant single crystalline structure in their respective directions in terms of minimum unit. "β" denotes an angle of a hollow portion defined in the structure having a substantially rectangular shape in plan view. "C2/m(#12)" indicates that it is the twelfth space group of the crystalline structure. "Monoclinic Z=2" indicates that the structure is monoclinic and two molecules are included in a unit cell. The overall precision of the analysis result is shown in terms of R factor. Specifically, a residual error between the structure factor calculated based on the analysis result and the actually observed structure factor is shown in terms of R factor.

Figure 8:
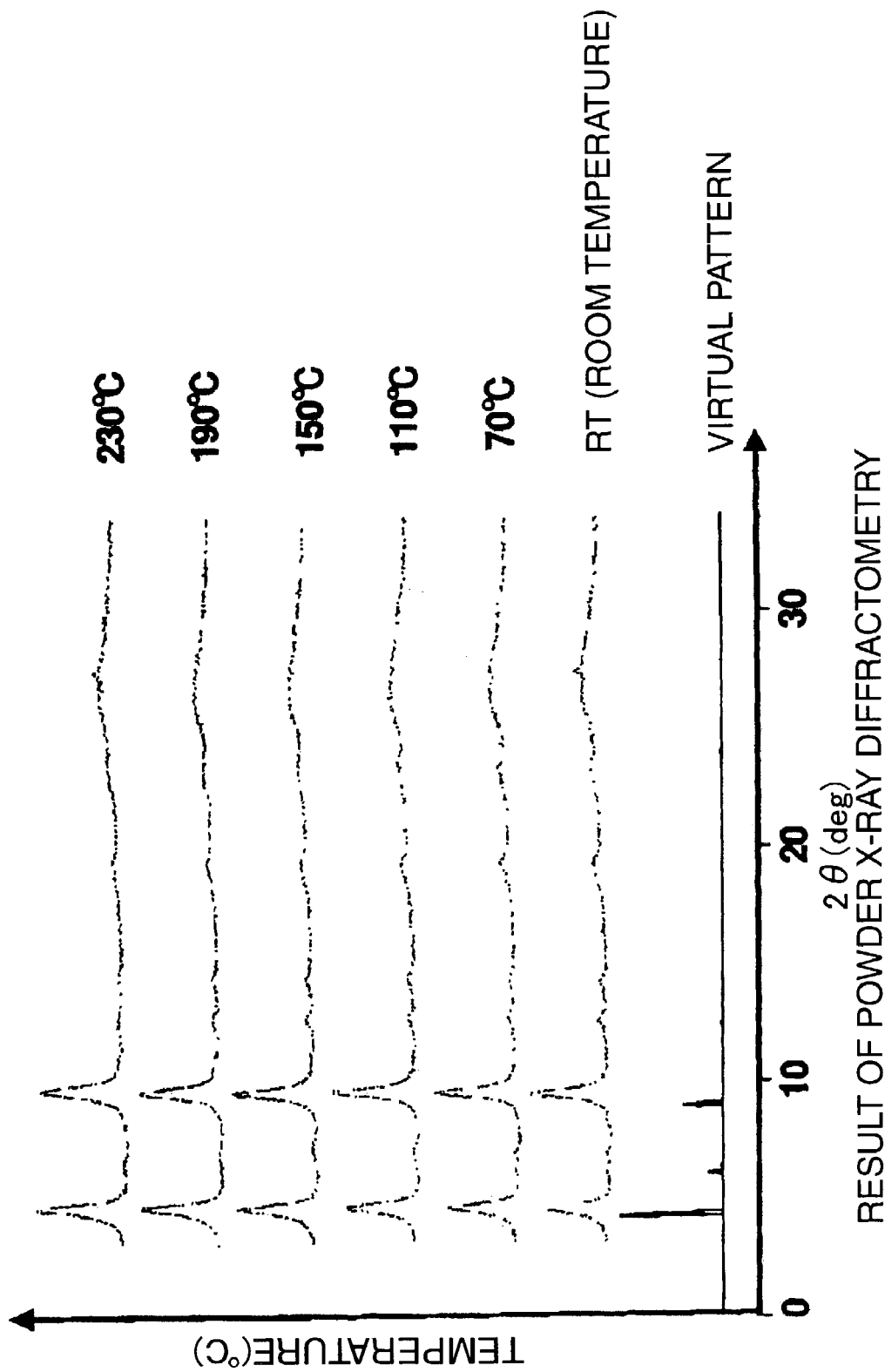
FIG. 8 is a chart showing results of powder X-ray diffractometry of the porous coordinatively unsaturated metal complex of this invention.
Figure 9:
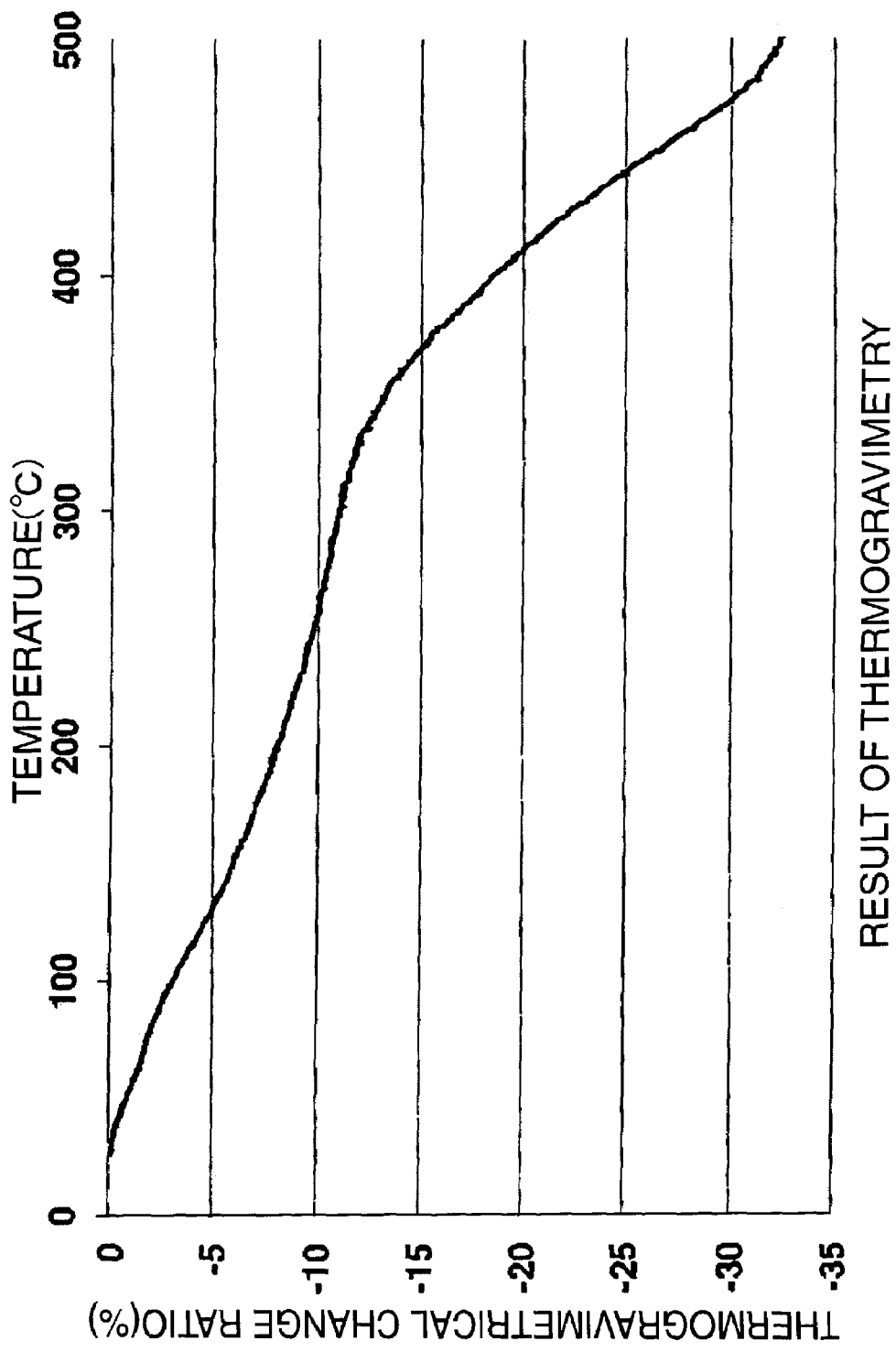
FIG. 9 is the result of thermogravimetry of the porous coordinatively unsaturated metal complex of this invention.

"Virtual pattern" in FIG. 8 is an idealistic pattern calculated based on the result of X-ray crystallographic analysis. The result given by FIG. 8 shows that the virtual pattern and the actually measured pattern were substantially the same. The result reveals that the measurement is in conformance with the calculation.

EXAMPLE 2

Example 2-1

Preparation of Metal Complex Unit in which Cobalt is Coordinatively Bounded

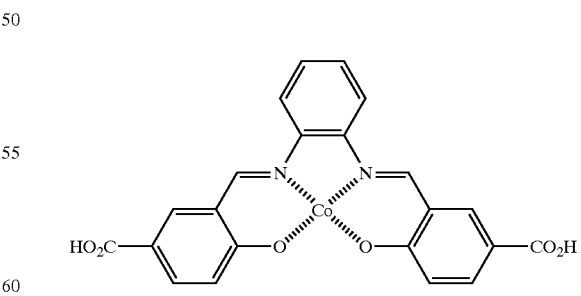

In 60 ml of dimethylformamide 11.0 g of the organic ligand of salen type obtained by Example 1-2 was dissolved, and the solution was stirred at room temperature under nitrogen atmosphere. To the solution, 30 ml of dimethylformamide solution containing 0.6 g of Cobalt (II) acetate was added dropwise.

After that, the solution was stirred for 1 hour, and the precipitate was removed by filtration. As a result of adding methanol to the filtrate, 1.0 g of brown solid was obtained.

Mass spectrum measurement was conducted with respect to the resultant product. The measurement result reveals that the peak of molecular ions of the product was 461.

Example 2-2

Production of the Porous Coordinatively Unsaturated Metal Complex (Cobalt Complex)

An experiment was conducted in the similar manner as Example 1-8 except that used was 0.1 g of the metal complex unit obtained in Example 2-1 in which cobalt (II) has been coordinatively bound, in place of the metal complex unit in which copper (II) has been coordinatively bound.

Figure 10:
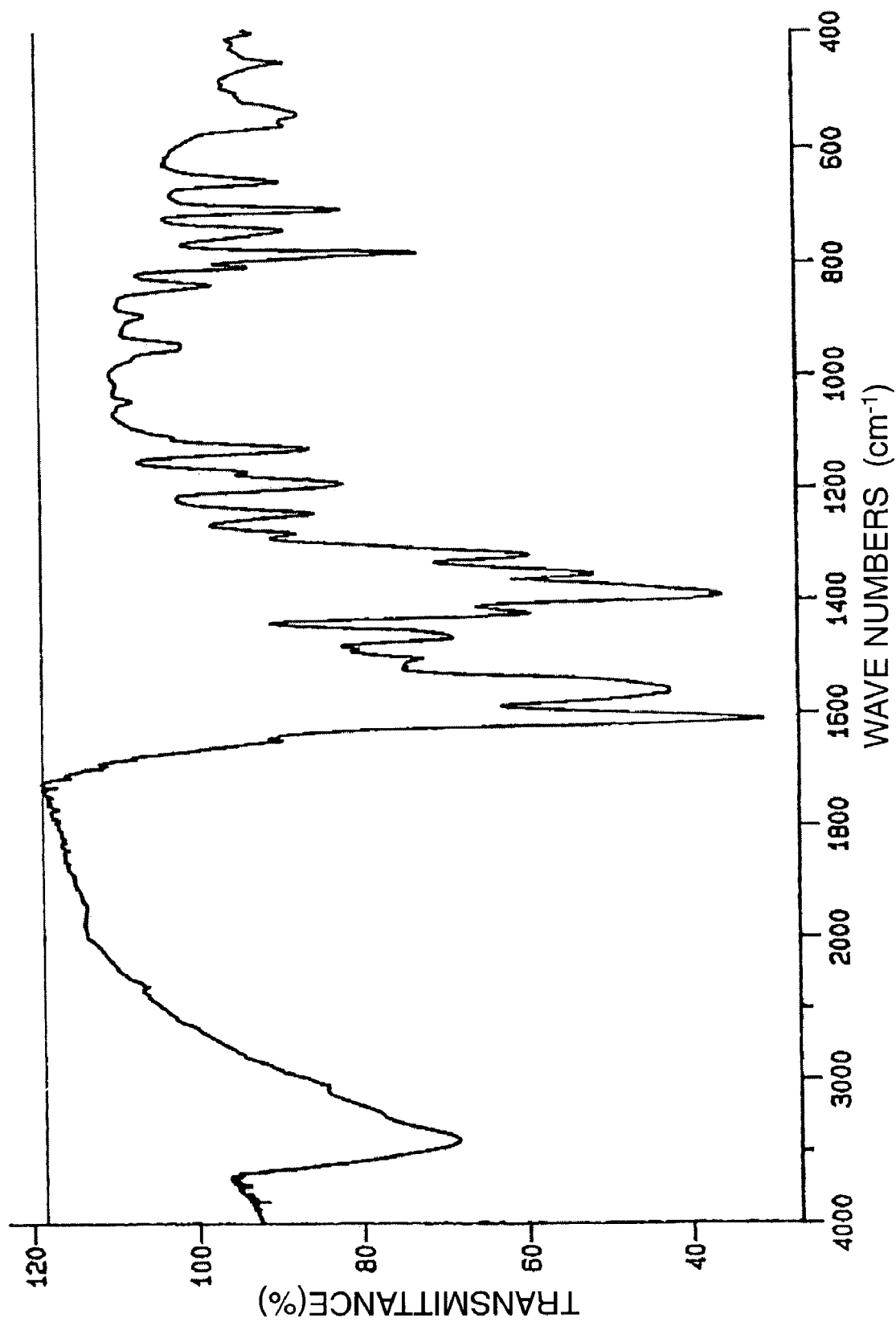
FIG. 10 is a chart showing a result of IR measurement of the product obtained in Example 2-2 of this invention.
Figure 11:
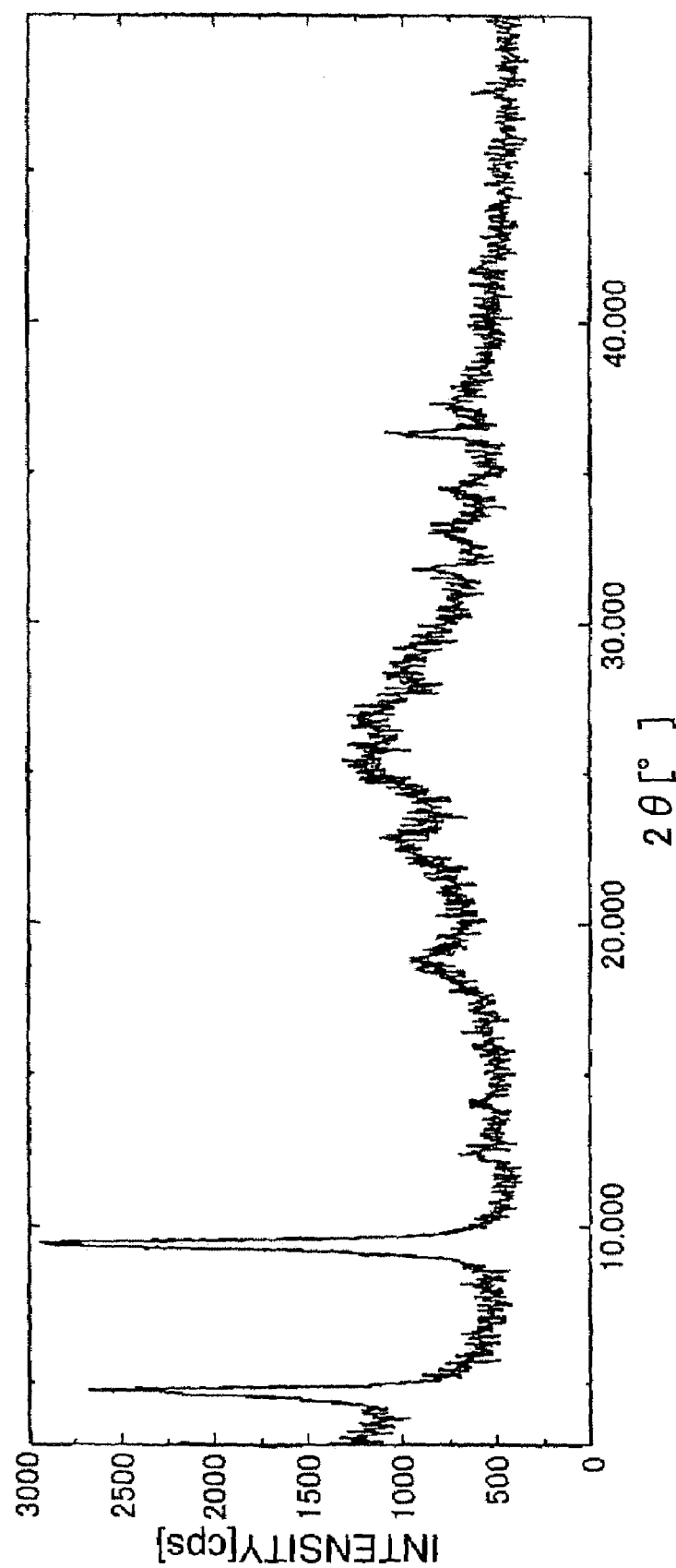
FIG. 11 is a chart showing a result of powder X-ray diffractometry of the porous coordinatively unsaturated metal complex obtained by Example 2-2.

As a result of the experiment, a target compound (single crystalline structure) was obtained. IR measurement (see FIG. 10) and powder X-ray diffractometry (see FIG. 11) were performed.

Example 2-3

Second Process for Producing the Porous Coordinatively Unsaturated Metal Complex (Cobalt Complex)

In 2 ml of dimethylformamide 0.05 g of the metal complex unit obtained in Example 2-1 in which cobalt (II) has been coordinatively bound was dissolved. To the solution, 1 ml of a dimethylformamide solution containing 0.16 mol/L of zinc nitrate (product of Wako Pure Chemicals Industries, Ltd.) was added, and then, 50 µl of triethylamine and 1 ml of water were added. And the total mixture was sealably put in an autoclave of which volume is 20 ml. After nitrogen replacement was fully conducted in the autoclave, the autoclave is pressurized at 0.16 MPa, and the mixture was heated at 110° C. for 5 hours.

After letting the mixture stand to cool, powder X-ray diffractometry was conducted. As a result of the analysis, the peak of molecular ions similar to that in Example 2-2 was observed.

EXAMPLE 3

Oxidation Reaction in which the Porous Coordinatively Unsaturated Metal Complex is Used as Catalyst In the autoclave (product of SUS) of which volume is 20 ml, 50 mg of the cobalt (II)-containing porous coordinatively unsaturated metal complex obtained in Example 2-3, 0.5 g of hydroquinone, and 5 ml of benzene were added. And the mixture was reacted while being stirred at 50° C. for 3 hours under pressurization of 1.47 MPa of nitrogen and 1.47 MPa of oxygen (both in the unit of gauge pressure).

After letting the mixture stand to cool to room temperature, the resultant liquid was analyzed according to gas chromatography. The result of the analysis reveals that inversion rate of hydryquinone is 30.8 mol %, and benzoquinone was obtained at yield of 25.9%.

EXAMPLE 4

Production of the Porous Coordinatively Unsaturated Metal Complex (Nickel Complex)

A solution in which 115.0 mg of the metal complex unit obtained in Example 1-5 in which nickel (II) has been coordinatively bound was dispersed in 20 ml of dimethylformamide, and a solution in which 112.0 mg of zinc nitrate hexahydrate was dissolved in 20 ml of a dimethylformamide were mixed. To the mixture 10 ml of water was added, and the mixture was put in a pressure-tight vessel. The vessel was brought to a sealed state after subjecting the mixture to bubbling nitrogen at room temperature for 10 minutes. After sealing, the vessel is pressurized at 0.16 MPa, and the mixture was heated at 100° C. for 8 hours for reaction.

After the reaction, powder X-ray diffractometry was conducted. As a result of analysis, the peak of molecular ions similar to that in Example 2-2 was observed.

COMPARATIVE EXAMPLE 1

Oxidation reaction of hydroquinone was conducted in the similar manner as Example 3 except that the porous coordinatively unsaturated metal complex containing cobalt (II) was not used. As a result of the experiment, benzoquine was obtained at such a low yield as 4.8%.

This application is based on Japanese patent application No. 2002-140495 and No. 2003-25182 filed on May 15, 2002 and Jan. 31, 2003 respectively, the contents of which are hereby incorporated by references.

As this invention may be embodied in several forms without departing from the spirit of essential characteristics thereof, the present embodiment is therefore illustrative an not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A porous coordinatively unsaturated metal complex comprising:
   a number of metal complex units and second metals,
   the each metal complex unit including a first metal and an organic ligand,
   the first metal being rendered to a coordinatively unsaturated state in the metal complex unit,
   the porous coordinatively unsaturated metal complex being structured by connecting the metal complex units one another through the second metals;
   the porous coordinatively unsaturated metal complex having voids;
   the voids having a size of 10 Å or more.

2. The porous coordinatively unsaturated metal complex according to claim 1, wherein at least one site of the organic ligand to which the first metal is to be coordinatively bound is a 15-group element of the periodic table.

3. The porous coordinatively unsaturated metal complex according to claim 1, wherein the organic ligand is a compound represented by the following formula (I):

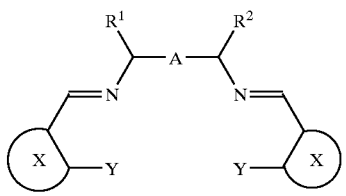

(I)

wherein:

"A" represents a single bond or a double bond, or may be absent;

"X" represents a $C_6$–$C_{10}$ monocyclic or a condensed aromatic hydrocarbon group which is substituted by 1 to 4 α groups described hereinbelow, or a nitrogen-containing heteroaryl group;

"Y" represents a hydroxyl group, an amino group, a thiol group, a di($C_1$–$C_6$alkyl)amino group, a di($C_1$–$C_6$alkyl) phosphino group, or a diarylphosphino group;

$R^1$ and $R^2$ are identical to or different from each other, and each represent a hydrogen atom, a $C_1$–$C_6$alkyl group, a $C_2$–$C_6$alkenyl group, a $C_1$–$C_6$alkoxy group, a halogen atom, a hydroxyl group, an amino group, a nitro group, or a cyano group, or $R^1$, $R^2$, carbon atoms respectively adjacent thereto, and "A" in the following partial integral structure:

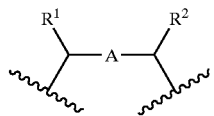

form a $C_6$–$C_{22}$ monocyclic or a condensed aromatic hydrocarbon group which may be substituted by 1 to 4 β groups described hereinbelow or a $C_3$–$C_6$ cyclic hydrocarbon group which may be substituted by 1 to 4 β groups described hereinbelow;

α is a group selected from the group consisting of a carboxyl group, a nitrogen-containing heteroaryl group, a di($C_1$–$C_6$ alkyl)phosphino group, a diarylphosphino group, a cyano group, a hydroxyl group, an amino group, and a thiol group; and β is a group selected from the group consisting of a $C_1$–$C_6$ alkyl group, a $C_1$–$C_6$ alkoxy group, a halogen atom, a hydroxyl group, an amino group, a nitro group, and a cyano group.

4. A process for producing a porous coordinatively unsaturated metal complex of claim 1, the process comprising steps of:

reacting the organic ligand with the first metal to prepare the metal complex unit in which the first metal is supported in a coordinatively unsaturated state, the organic ligand having two coordination donors with a distance between the coordination donors of 10 Å or more; and mixing the metal complex units or a solution containing the metal complex units with the second metals or a solution containing the second metals to connect the metal complex units one another through the second metals.

5. A method of catalyzing a reaction using a porous coordinatively unsaturated metal complex of claim 1, comprising reacting the porous coordinatively unsaturated metal complex according to claim 1 with a starting material to produce a product, wherein the reaction to be catalyzed is the oxidation of an aromatic alcohol.

* * * * *